(12) United States Patent
Funk et al.

(10) Patent No.: US 7,542,859 B2
(45) Date of Patent: *Jun. 2, 2009

(54) CREATING A VIRTUAL PROFILE LIBRARY

(75) Inventors: Merritt Funk, Austin, TX (US); Daniel J. Prager, Hopewell Junction, NY (US)

(73) Assignee: Tokyo Electron Ltd., Tokyo (JP)

( * ) Notice: Subject to any disclaimer, the term of this patent is extended or adjusted under 35 U.S.C. 154(b) by 248 days.

This patent is subject to a terminal disclaimer.

(21) Appl. No.: 11/394,859

(22) Filed: Mar. 31, 2006

(65) Prior Publication Data
US 2007/0239369 A1 Oct. 11, 2007

(51) Int. Cl.
*G01R 13/00* (2006.01)
(52) U.S. Cl. .................................................. 702/71
(58) Field of Classification Search .............. 702/71, 702/80, 189
See application file for complete search history.

(56) References Cited

U.S. PATENT DOCUMENTS

| | | | |
|---|---|---|---|
| 6,609,086 B1 | 8/2003 | Bao et al. | |
| 6,636,843 B2 | 10/2003 | Doddi et al. | |
| 6,768,983 B1 | 7/2004 | Jakatdar et al. | |
| 6,785,638 B2 | 8/2004 | Niu et al. | |
| 7,126,700 B2 | 10/2006 | Bao et al. | |
| 7,305,322 B2 * | 12/2007 | Funk et al. | 702/155 |
| 7,451,054 B2 * | 11/2008 | Deshpande et al. | 702/134 |
| 7,487,053 B2 * | 2/2009 | Funk et al. | 702/66 |
| 2001/0051856 A1 | 12/2001 | Niu et al. | |
| 2008/0183411 A1 * | 7/2008 | Funk et al. | 702/84 |

OTHER PUBLICATIONS

Least Mean Square Algorithm, Widrow et al., 1959.*
Yale University, "Chi-Square Goodness of Fit Test", 1997-1998.*

* cited by examiner

*Primary Examiner*—Michael P Nghiem
(74) *Attorney, Agent, or Firm*—Morrison & Foerstar LLP

(57) ABSTRACT

A method of creating a virtual profile library includes obtaining a reference signal. The reference signal is compared to a plurality of signals in a first library. The reference signal is compared to a plurality of signals in a second library. A virtual profile data space is created when first and second matching criteria are not met. The virtual profile data space is created using differences between a profile data spaces associated with the first and second libraries. A first virtual profile signal is created in the virtual profile data space. A difference is calculated between the reference signal and the first virtual profile signal. The difference is compared to a virtual profile library creation criteria. If the virtual profile library creation criteria is met, the first virtual profile signal and the virtual profile data, associated with the first virtual profile signal is stored.

34 Claims, 20 Drawing Sheets

CREATING A VIRTUAL PROFILE LIBRARY

BACKGROUND

1. Field

The present application generally relates to integrated circuit (IC) metrology, and, more particularly, to the creation of virtual profile libraries or virtual profile data spaces to use in determining the critical dimensions (CD's) and profiles of IC structures.

2. Description of the Related Art

With the current drive towards smaller geometries of IC features, features measurement is increasingly difficult as the size of the features become smaller. However, knowledge of the dimensions of gratings or periodic structures is essential in order to determine if the dimensions of the features are within the acceptable ranges and if a particular fabrication process causes the sidewalls of the features to be tapered, vertical, T-topped, undercut, or have footings.

Traditionally, a sample was cleaved and examined with a scanning electron microscope (SEM) or similar device. The cross-section SEM method is typically slow, expensive, and destructive whereas the CD SEM method only provides one measurement number seen from the top of the feature. Spectroscopic reflectometry and ellipsometry are used to beam light on the structure and measure the spectrum of reflected signals. Current practices basically use an empirical approach where the spectra of reflected light is measured for a known width of features in a structure. This process is time consuming and expensive even for a limited library of profiles of structure dimensions and the associated spectrum data of reflected/diffracted light. Furthermore, if such a library were built for a wide range of profiles at a fine resolution, the process of building the library is time consuming and cost-prohibitive. With IC features becoming smaller, there is a need for a library with even finer resolution. As the resolution of the library increases, the size of the library increases while the time to create the library increases exponentially. Furthermore, an extensive library of profiles and spectra is inefficient for searching purposes, especially for real-time work. Thus, there is a need for a method, system, and/or apparatus that facilitates the use of metrology devices and systems for measuring profiles without creating huge profile libraries or data collections and incurring extensive searches of said profile libraries or data collections.

SUMMARY

In one exemplary embodiment, a method of creating a virtual profile library includes obtaining a reference signal. The reference signal was generated by measuring a signal off a reference structure on a semiconductor wafer with a metrology device. The reference signal is compared to a plurality of signals in a first library. The comparison is stopped if a first matching criteria is met. The reference signal is compared to a plurality of signals in a second library. The comparison is stopped if a second matching criteria is met. A virtual profile data space is created when the first and second matching criteria are not met. The virtual profile data space is created using differences between a profile data space associated with the first library and a profile data space associated with the second library. A first virtual profile signal is created in the virtual profile data space. A virtual profile shape and/or virtual profile parameters is created based on the first virtual profile signal. A difference is calculated between the reference signal and the first virtual profile signal. The difference is compared to a virtual profile library creation criteria. If the virtual profile library creation criteria is met, the first virtual profile signal and the virtual profile data, which includes the virtual profile shape and/or virtual profile parameters, associated with the first virtual profile signal is stored. Or, if the virtual profile library creation criteria is not met, a corrective action is applied.

BRIEF DESCRIPTION OF THE DRAWINGS

Exemplary embodiments will now be described, by way of example only, with reference to the accompanying schematic drawings in which corresponding reference symbols indicate corresponding parts, and in which:

FIG. 10B illustrates another exemplary view of a virtual profile data space in accordance with embodiments of the invention;

FIG. 13A is an architectural diagram illustrating a system for creating, refining, and/or using a virtual profile library in accordance with embodiments of the invention; and.

DETAILED DESCRIPTION

This application relates to U.S. patent application Ser. No. 11/396,112, entitled USING A VIRTUAL PROFILE LIBRARY, filed on Mar. 31, 2006; now issued as U.S. Pat. No. 7,305,322; and U.S. patent application Ser. No. 11/394,860, entitled REFINING A VIRTUAL PROFILE LIBRARY, filed on Mar. 31, 2006, now issued as U.S. Pat No. 7,487,053. The contents of each of these applications are herein incorporated by reference in their entireties.

This application also relates to U.S. patent application Ser. No. 09/727530, entitled SYSTEM AND METHOD FOR REAL-TIME LIBRARY GENERATION OF GRATING PROFILES, by Jakatdar, et al., filed on Nov. 28, 2000, now issued as U.S. Pat. No. 6,768,983; to U.S. patent application Ser. No. 09/764,780, entitled CACHING OF INTRA-LAYER CALCULATIONS FOR RAPID RIGOROUS COUPLED-WAVE ANALYSES, by Niu, et al., filed on Jan. 25, 2001, now abandoned; to U.S. patent application Ser. No. 09/737,705, entitled SYSTEM AND METHOD FOR GRATING PROFILE CLASSIFICATION, by Doddi, et al., filed on Dec.14, 2000, now issued as U.S. Pat. No. 6,636,843; and to U.S. patent application Ser. No. 09/923,578, entitled METHOD AND SYSTEM OF DYNAMIC LEARNING THROUGH A REGRESSION-BASED LIBRARY GENERATION PROCESS, filed Aug. 6, 2001, now issued as U.S. Pat. No. 6,785,638. The contents of each of these applications are herein incorporated by reference in their entireties.

In order to facilitate the description of the present invention, an optical metrology system is used to illustrate the concepts and principles. It is understood that the same concepts and principles equally apply to the other IC metrology systems as will be discussed below. In a similar manner, although a virtual profile library is frequently used to illustrate concepts and principles, the present invention equally applies to a data space comprising virtual profile parameters and corresponding virtual profile signals.

Figure 1:
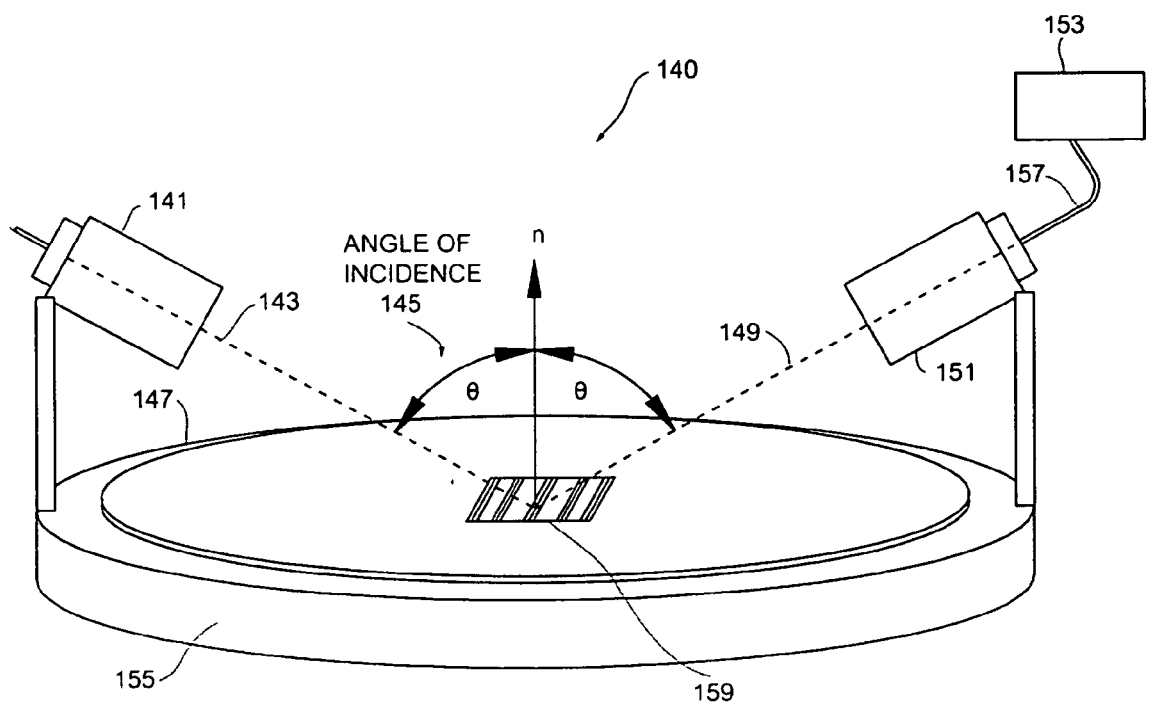
FIG. 1 is an architectural diagram illustrating the use of optical metrology to measure the diffracted spectra off integrated circuit periodic structures.

FIG. 1 is an architectural diagram illustrating the use of optical metrology to measure the diffracted spectra off integrated circuit periodic structures. The optical metrology system 140 includes a metrology beam source 141 projecting a beam 143 at the target periodic structure 159 of a wafer 147 mounted on a metrology platform 155. The metrology beam 143 is projected at an incidence angle Θ towards the target periodic structure 159. The diffracted beam 149 is measured by a metrology beam receiver 151. The diffracted beam data 157 is transmitted to a metrology profiler system 153. The metrology profiler system 153 compares the measured diffracted beam data 157 against a library of calculated diffracted beam data representing varying combinations of profile parameters of the target periodic structure and resolution. The library instance best matching the measured diffracted beam data 157 is selected. The profile and associated critical dimensions of the selected library instance correspond to the cross-sectional profile and critical dimensions of the features of the target periodic structure 159. The optical metrology system 140 may utilize a reflectometer, an ellipsometer, or other optical metrology device to measure the diffracted beam or spectrum. An optical metrology system is described in U.S. patent application Ser. No. 09/727,530 now U.S. Pat. No. 6,768,983, entitled SYSTEM AND METHOD FOR REAL-TIME LIBRARY GENERATION OF GRATING PROFILES, by Jakatdar, et al., filed on Nov. 28, 2000, and is incorporated in its entirety herein by reference.

Figure 2A:
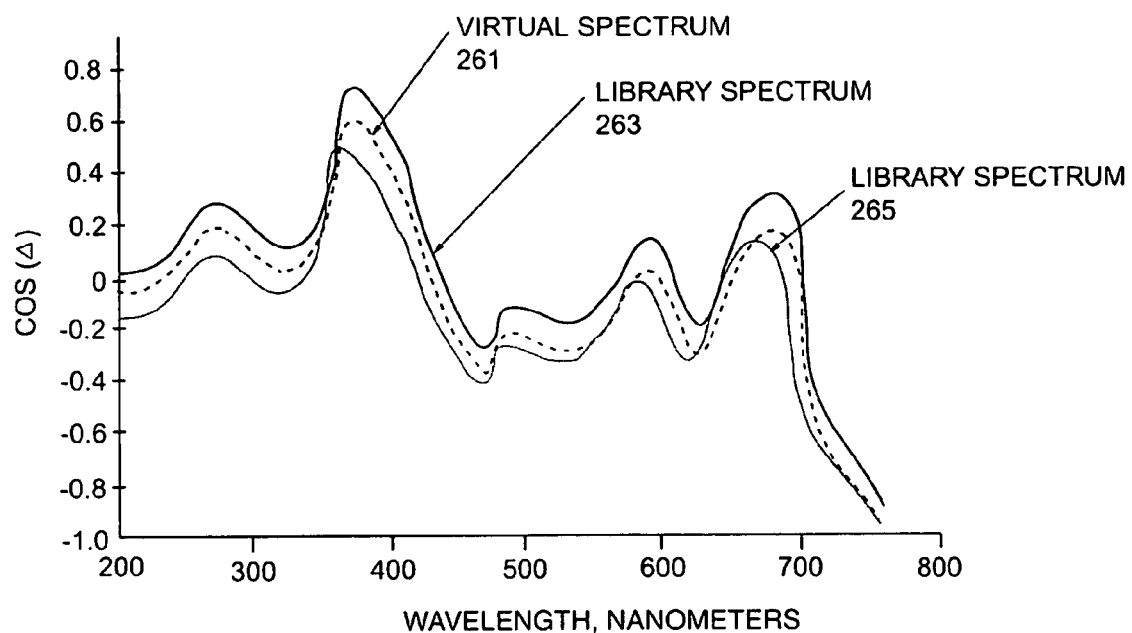
FIG. 2A illustrates a measured diffracted spectrum graph compared to diffracted spectra graphs of instances in a profile library.

FIG. 2A illustrates a virtual spectrum 261 compared to two library spectra 263 and 265. As will be described in greater detail below, library spectra 263 and 265 can be obtained from one or more libraries, and virtual spectrum 261 can be calculated from library spectra 263 and 265. In one exemplary embodiment, virtual spectrum 261 is calculated based on the difference between library spectra 263 and 265. Virtual spectrum 261 can be stored as an instance in a virtual profile library. Any number of virtual spectra 261 can be generated and stored as instances in the virtual profile library.

In FIG. 2A, the wavelength in nanometers (nm) is shown in the X-axis and cosine (Δ), an ellipsometric measurement of the diffracted spectrum, in the Y-axis. A virtual profile library can be created with ranges of CD's and other profile parameters of structures in a wafer. The number of instances of the virtual profile library can be a function, of the combinations of the various CD's and other profile parameters, at the specified resolution. For example, the range of the top CD for a structure may be from 100 to 300 nm and the specified resolution is 10 nm. In combination with the other profile parameters of the structure, one or more instances of the virtual profile library can be created starting at 100 nm top CD and for every 10 nm increment thereafter until 300 nm. For a detailed description of parameters used to create a profile library, refer to U.S. patent application Ser. No. 09/727,530 now U.S. Pat. No. 6,768,983, entitled SYSTEM AND METHOD FOR REAL-TIME LIBRARY GENERATION OF GRATING PROFILES, by Jakatdar, et al., filed on Nov. 28, 2000, which is incorporated herein by reference. For example, instances of a virtual profile library for trapezoidal profiles may have diffracted spectra and profile parameters including a top CD, a bottom CD, and height.

In FIG. 2A, library spectrum (a first signal) 263 corresponding to a first set of the profile parameters at a given resolution and library spectrum (a second signal) 265 corresponding to a second set of profile parameters at the same resolution are illustrated. The first signal 263 can be associated with a first library, and the second signal 265 can be associated with a second library. Alternatively, the first and second signals may be associated with the same library. In addition, virtual spectrum (a calculated virtual profile signal) 261 is shown in close proximity to the first signal 263 and the second signal 265. In various embodiments, the virtual profile signal 261 can be determined using the first signal 263, the second signal 265, or both signals. For example, the calculated virtual profile signal 261 can be determined using a difference between the first signal 263 and the second signal 265. In addition, virtual profile shapes and virtual profile parameters can be determined using the virtual profile signal such as shown in FIG. 2A.

Figure 2B:
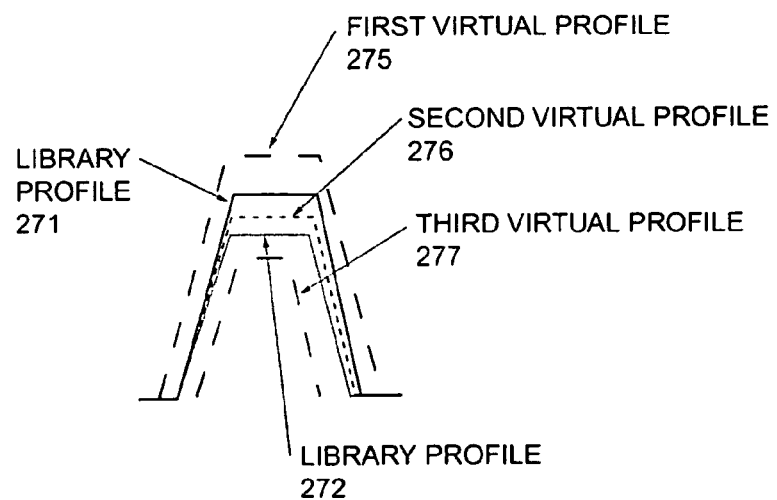
FIG. 2B illustrates a structure profile of a measured periodic structure compared to profiles of instances in a profile library.

FIG. 2B illustrates library profiles (also referred to as hypothetical profiles), which characterize profiles of structures to be formed on a wafer, in accordance with embodiments of the invention. In the illustrated embodiment, a first profile 271 of a trapezoidal structure, a second profile 272 of a second trapezoidal structure are illustrated. The trapezoidal structures are shown for illustration and are not required for the invention. The library profiles can include multiple shapes in multiple layers. In addition, three virtual profiles 275, 276, and 277 having trapezoidal structures are illustrated. The virtual profiles 275, 276, and 277 can have similar shapes. The virtual profiles 275, 276, and 277 can be established based on one or more differences between the first and second profiles. Differences can be calculated at different wavelengths or different groups of wavelengths. The first profile 271 can be associated with a first library, and the second profile 272 can be associated with a second library. Alternatively, the first and second profiles may be associated with the same library. For example, the first profile 271 may be associated with the first signal 263; the second profile 272 may be associated with the second signal 265; and one of the virtual profiles 275, 276, and 277 may be associated with the virtual profile signal 261. Alternatively, different signals, different shapes, and/or different associations may be used. In some embodiments, the libraries can include a "612 nm" library, a "395 nm" library, and/or a "245 nm" library. Alternatively, other libraries may be used.

Virtual profile libraries can be used to extend the usefulness (range) of existing or measured libraries. In various embodiments, virtual profile shapes and virtual profile parameters can be determined that correspond to the virtual profile signal (spectrum), the determination can be based on the virtual spectrum and on data selected from existing libraries or on data derived using simulation techniques. In addition, virtual profile library data, which can include the virtual profile signal, the virtual profile shape, and/or the virtual profile parameters, can be created using signals, such as shown in FIG. 2A, and profiles, such as shown in FIG. 2B along with "best match" and/or "best estimate" algorithms. However, these techniques may produce unrefined data having a certain amount of inaccuracy. One solution may be to perform a refinement procedure thereby increasing the resolution of a refined virtual library. However, this can increase the size of the library, which has the disadvantage of more time and computation to generate the library, to store the library, and to search the library. As such, in the exemplary embodiments described below, virtual profile library procedures can be performed in real-time to create, refine, and/or use virtual profile data that can be based on the newly created virtual profile library data, existing library spectra/profiles, simulated spectrum, and the measured spectrum.

Existing libraries can include data for isolated and nested structures, and virtual profile libraries can also include data for isolated and nested structures.

Figure 3A:
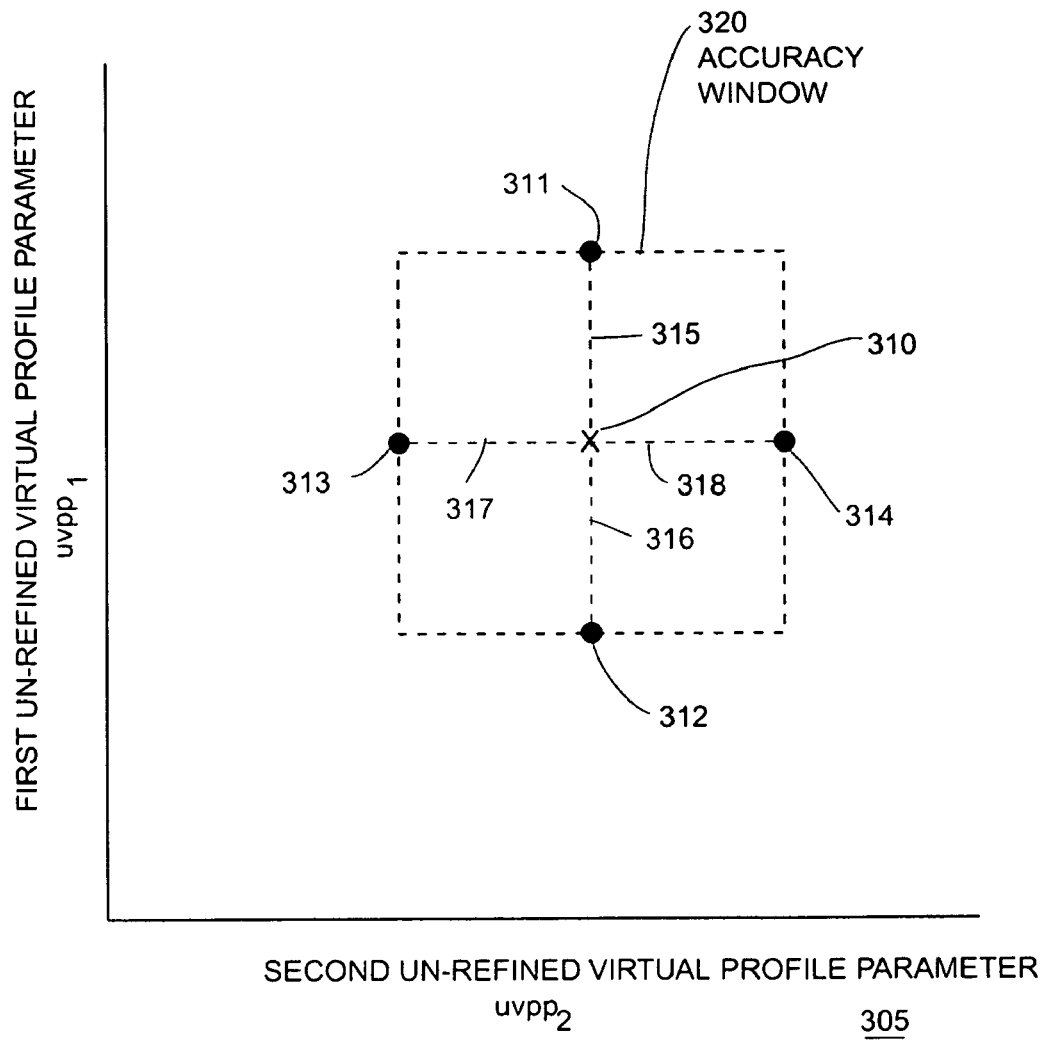
FIG. 3A illustrates an exemplary view of an un-refined virtual profile data space in accordance with embodiments of the invention.

FIG. 3A illustrates an un-refined virtual data space in accordance with embodiments of the invention. In the illustrated embodiment, an un-refined virtual data space 305 is shown and can be defined using a first un-refined virtual profile parameter ($uvpp_1$) and a second un-refined virtual profile parameter ($uvpp_2$). A first data point 310 is illustrated in the unrefined virtual data space 305. The first data point can be associated with a first un-refined virtual profile and/or unrefined virtual profile signal. The first data point is shown along with accuracy limits 311, 312 for the first un-refined virtual profile parameter ($uvpp_1$) and accuracy limits 313, 314 for the second un-refined virtual profile parameter ($uvpp_2$). The accuracy limits 311, 312 can be established using tolerance values 315, 316 for the first un-refined virtual profile parameter ($uvpp_1$) and accuracy limits 313, 314 can be established using tolerance values 317, 318 for the second un-refined virtual profile parameter ($uvpp_2$). The accuracy limits (311, 312, 313, and 314) and/or tolerance limits (315, 316, 317, and 318) can be known values. Alternatively, the accuracy limits (311, 312, 313, and 314) and/or tolerance limits (315, 316, 317, and 318) may have unknown values. In addition, an accuracy window 320 is shown surrounding the first unrefined data point 310. For example, uvpp1 can be a bottom CD and uvpp2 can be a top CD for a structure. The bottom CD may be calculated using the difference between a bottom CD in one library and a bottom CD in another library, and the top CD may be calculated using the difference between a top CD in one library and a top CD in another library. In addition, the accuracy and/or tolerance values for the virtual profile parameters can be based on the accuracy and/or tolerance values associated with the libraries used during the calculations. In this example, if the top CD and bottom CD have tolerances of 4 nm, then the $uvvp_1$ and $uvpp_2$ may have tolerances that are equal to or greater than 4 nm depending on a confidence value associated with the calculation.

The unrefined virtual data space 305 can be established during the creation of an unrefined virtual profile library creation procedure. In addition, the unrefined virtual data space 305 can include other data points (not show). The accuracy limits (311, 312, 313, and 314) and/or tolerance limits (315, 316, 317, and 318) can be examined to determine if the limits are within the limits required for a refined virtual profile library. In some cases, the accuracy associated with the unrefined data space is not within specified limits, a refinement procedure may be required. In other cases, the accuracy associated with the unrefined data space is within specified limits, and a refinement procedure may not be required.

Figure 3B:
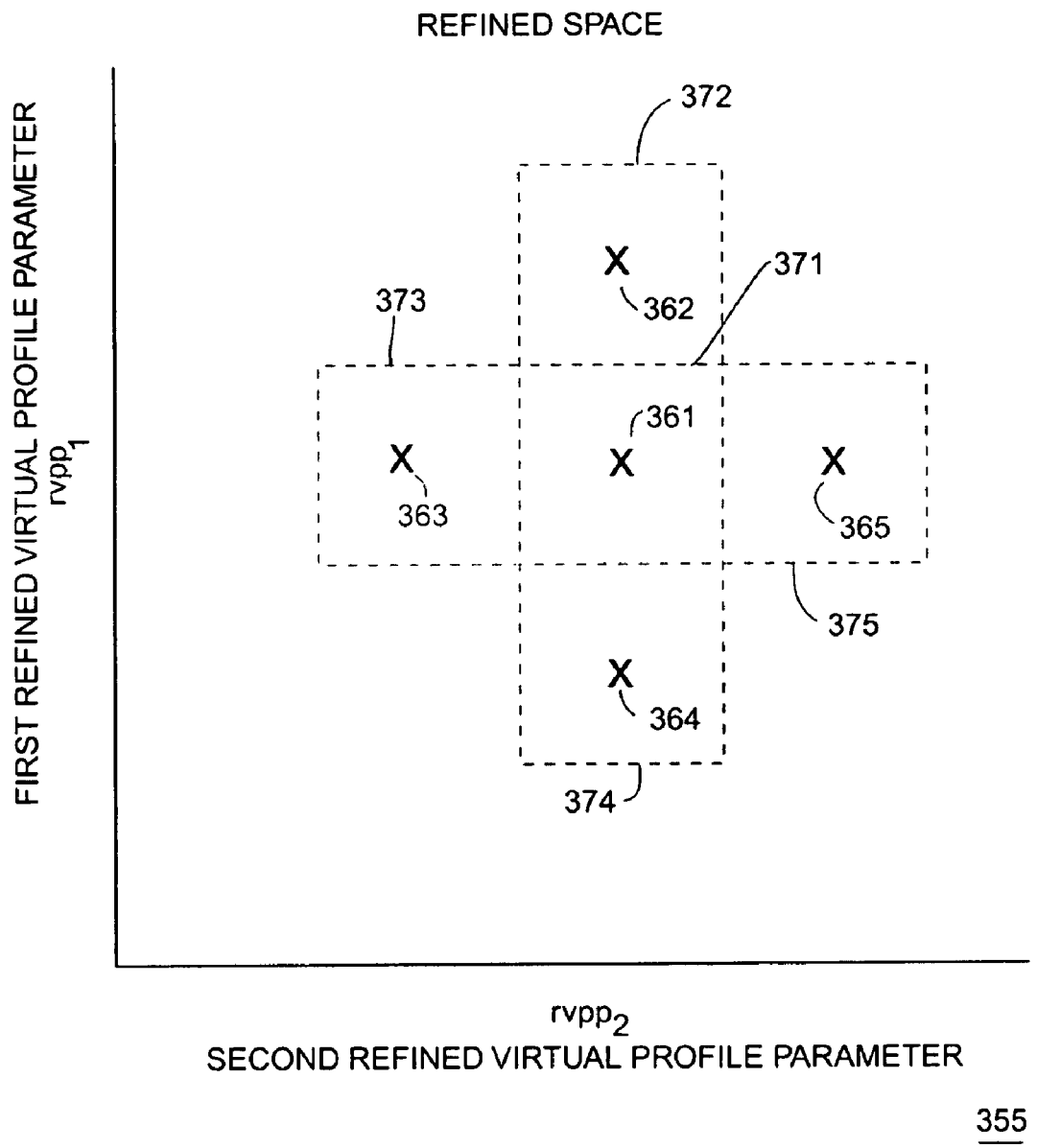
FIG. 3B illustrates an exemplary view of a refined virtual profile data space in accordance with embodiments of the invention.

FIG. 3B illustrates a refined virtual data space in accordance with embodiments of the invention. In the illustrated embodiment, a refined virtual data space 355 is shown that can be defined using a first refined virtual profile parameter ($rvpp_1$) and a second refined virtual profile parameter ($rvpp_2$). A first data point 361 is illustrated in the refined virtual data space 355. The first data point can be associated with a first refined virtual profile and/or refined virtual profile signal. The first data point 361 is shown along with an accuracy window 371 and the size of the accuracy window can be determined using the specified accuracy limits for the first refined virtual profile parameter ($rvpp_1$) and specified accuracy limits for the second refined virtual profile parameter ($rvpp_2$). The specified accuracy limits can be established using virtual profile creation criteria, and can be established to ensure accurate virtual profile libraries. For example, business rules may be used to establish some of the virtual profile creation criteria. In addition, a second accuracy window 372 is shown surrounding a second refined data point 362, a third accuracy window 373 is shown surrounding a third refined data point 363, a fourth accuracy window 374 is shown surrounding a fourth refined data point 364, and a fifth accuracy window 375 is shown surrounding a fifth refined data point 365.

For example, rvpp1 can be a refined value for a bottom CD and rvpp2 can be a refined value for a top CD for a structure. A refine procedure can be performed to obtain the refined values. The top CD and bottom CD can have refined tolerances of 1 nm. In one embodiment, the accuracy window size can be determined to ensure that the entire refined virtual profile data space is defined. In a well-defined virtual profile data space, overlapping windows and undefined spaces are avoided.

The refined data space 355 can be established by using a refinement (accuracy improvement) procedure during a virtual profile library creation procedure. In some embodiments, the accuracy associated with the unrefined data space is unknown or greater than a desired value, and a refinement procedure can be performed to create a refined virtual profile library that includes refined virtual profiles and refined virtual profile signals.

In general terms, a data point is a set of profile parameters with an associated spectrum, and sets of profile parameters and associated spectra can be organized in the form of a library. In addition, the term library data point can be used. It should be understood that the principles and concepts of the present invention would apply regardless of the method of organizing the data. A set of data points can be a profile data space or data space in short. These terms can be used to describe un-refined and/or refined data items.

During processing, a wafer can be sent to a metrology tool for evaluation. For example, a wafer can be sent to a metrology tool to verify data determined using a CDSEM. A wafer can be sent to a metrology tool to establish wafer state data that can be fed forward and/or fed back to change and/or verify a process recipe.

A processing system and/or processing tool can receive metrology data and/or recipes from the metrology tool. A processing system and/or processing tool can provide metrology data and/or recipes to the metrology tool. In various embodiments, the processing system can include etch tools/modules, cleaning tools/modules, deposition tools/modules, "track" tools/modules, scanning tools/modules, exposure tools/modules, photoresist processing tools/modules, and thermal processing tools/modules.

Figure 3C:
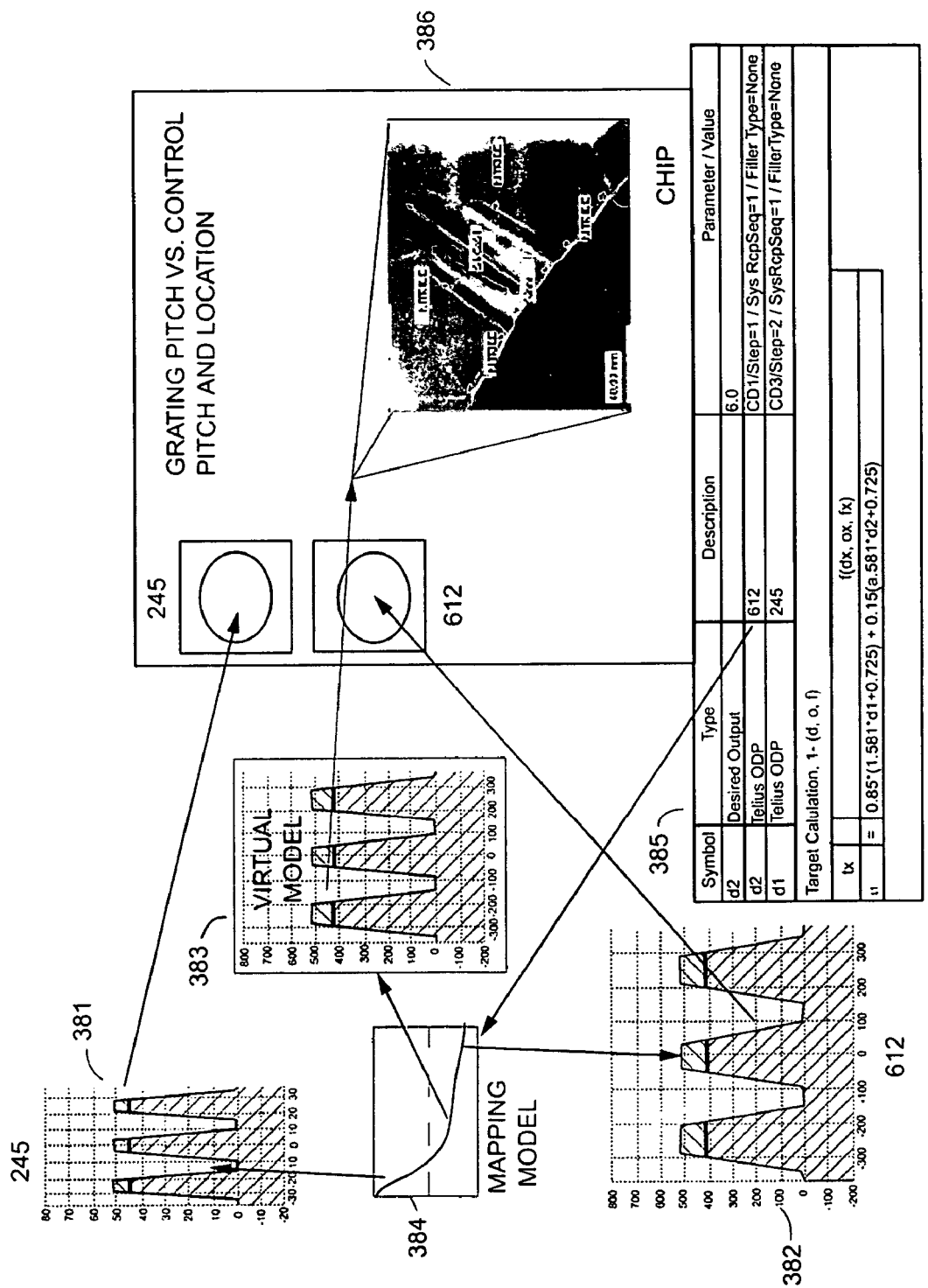
FIG. 3C illustrates an exemplary view of a mapping process for creating virtual profile data in accordance with embodiments of the invention.

FIG. 3C illustrates an exemplary view of a mapping process for creating virtual profile data in accordance with embodiments of the invention. In the illustrated embodiment, a first set of structures are shown in a "245" data space 381, a second set of structures are shown in a "612" data space 382, and a set of virtual structures are shown in a virtual profile data space 383. In one embodiment, a mapping model 384 can be developed using data from the "612" data space and data from the "245" data space, and a mapping model can be used to create virtual structures in a virtual profile data space. In addition, the mapping model can be used to modify recipes in a processing tool 385 and can be used to identify structure on a semiconductor chip 386.

For example, when fixed gratings are used on semiconductor wafers, measured data based on a fixed grating pitch may be different from the actual pitch of the structure being measured by the CDSEM or used for control. In one example, measurements can be taken using two gratings, one can be larger, and one can be smaller than the physical structure. A virtual profile model (matrix) can be developed based on CDSEM measurement of all three structures or a cross sectional SEM (or other respected reference metrology system). The virtual profile model may not be linear. The virtual profile model can be developed by performing a correlation exercise between each IM measured pitch and the intermediate pitch measured on CDSEM. Additionally, the correlation could be made between the intermediate pitch and only one of the more extreme pitches. The correlation could be done with any standard correlation technique.

The virtual profile mapping model can be multi-dimensional, and the mapping model can create virtual profile data in real-time. The virtual profile mapping model can be created using one or more libraries or as a simple CD scale factor. The virtual profile mapping model can be computed by a processing system or by a factory system and loaded in the control plan as two scaling factors.

In addition, multiple correlations can be done for multiple metrics of interest (CD, SWA, thickness). The virtual profile mapping model can be used to create an estimated profile for the intermediate measurement.

Figure 4A:
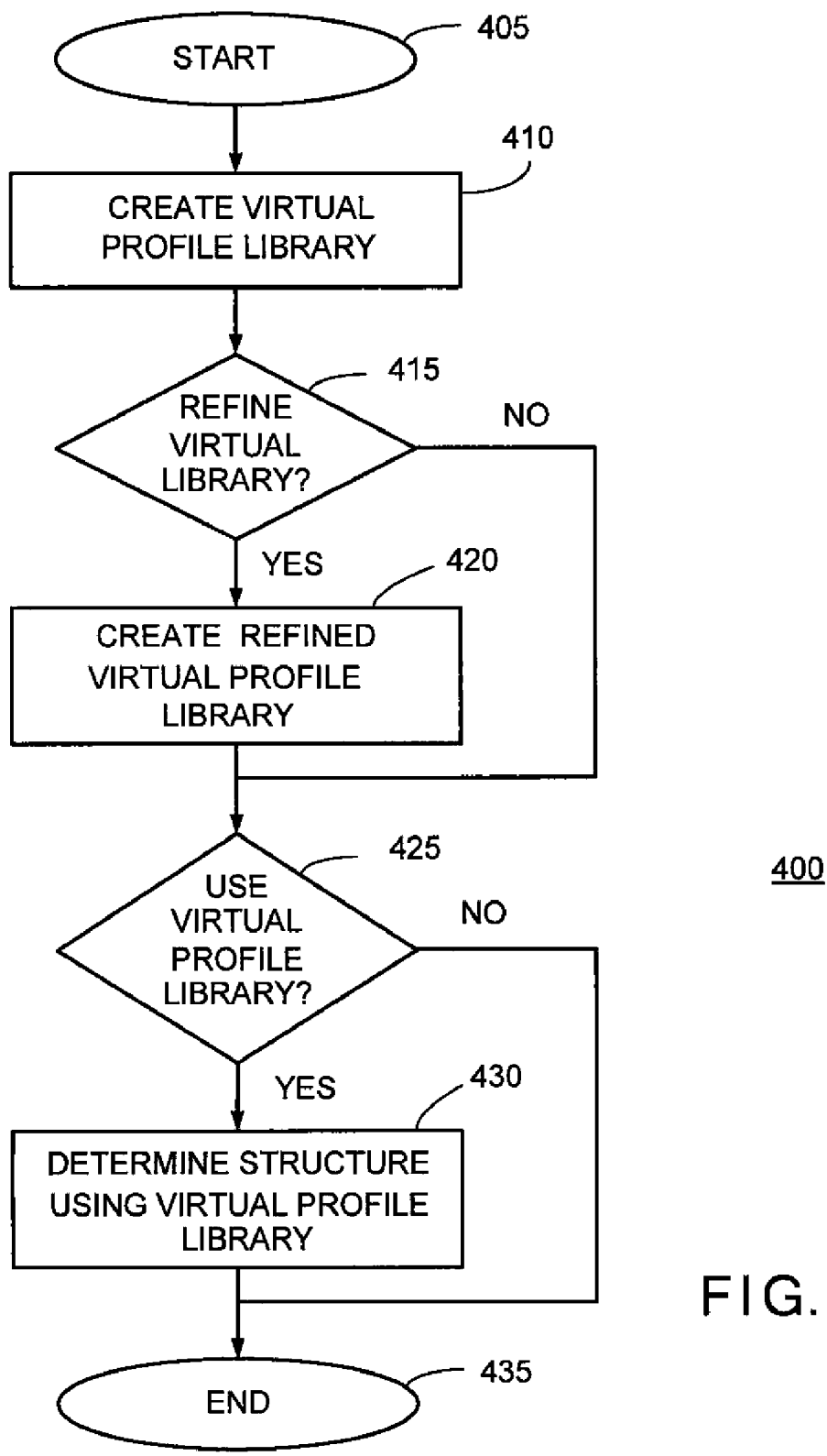
FIG. 4A illustrates a procedure for creating, refining, and/or using a virtual profile library in accordance with embodiments of the invention.

FIG. 4 illustrates a procedure for creating, refining, and/or using a virtual profile library in accordance with embodiments of the invention. In 405, procedure 400 can start. In 410, a virtual profile library can be created. In various embodiments, a new virtual profile library can created thereby providing a means for assessing new and/or unique structures. A virtual profile library can be refined, while it is being created or after it has been created, thereby providing a more accurate assessment of a structure. A virtual profile library can be used to identify structures and can provide process result data and recipe modification information to a processing tool. In some embodiments, "P-domain" data can be used to create a virtual profile library.

In one embodiment, a first profile in a first profile data space can be selected, and the first profile can have a first signal and a first set of profile parameters associated with it. The first profile data space can be associated with a first library containing previously measured profiles and associated signals. A second profile in a second profile data space can be selected, and the second profile can have a second signal and a second set of profile parameters associated with it. The second profile data space can be associated with a second library. Alternatively, the profile data spaces may be associated with the same library. Then, an un-refined virtual profile can be determined that corresponds to an un-refined virtual profile signal based on a difference between the first signal and the second signal, and the un-refined virtual profile can be defined by a set of un-refined virtual profile parameters.

Similar shaped profiles can be chosen and dimensional differences between similar shapes can be used to create virtual profiles. The dimensional differences can be average values. For example, a top CD in one library may be 10 nm, and the top CD in another library may be 8 nm. A virtual profile may be created with a top CD of approximately 9 nm. In this case, the difference can be divided by two. In another example, a top CD in one library may be 10 nm; a top CD in another library may be 8 nm, and a virtual profile may be created with a top CD of approximately 7 nm. In this case, a linear relationship can be used to create a virtual library with dimensions that are less than the other two libraries. In addition, a linear relationship can be used to create a virtual library with dimensions that are greater than the other two libraries. Alternatively, non-linear relationships may be used.

In alternate embodiments, the differences between diffracted signals and/or spectra can be used to create virtual profile library data. Alternatively, other types of signals may be used. The signals associated with the profiles in a library can be band-limited signals. For example, wavelengths between 100 nm and 1000 nm may be used. A bandwidth can be established for the comparison, and a number of comparison points can be established. For example, similar shaped profiles may be chosen and differences between the signals associated with the similar shapes can be used to create virtual profiles.

Figure 4B:
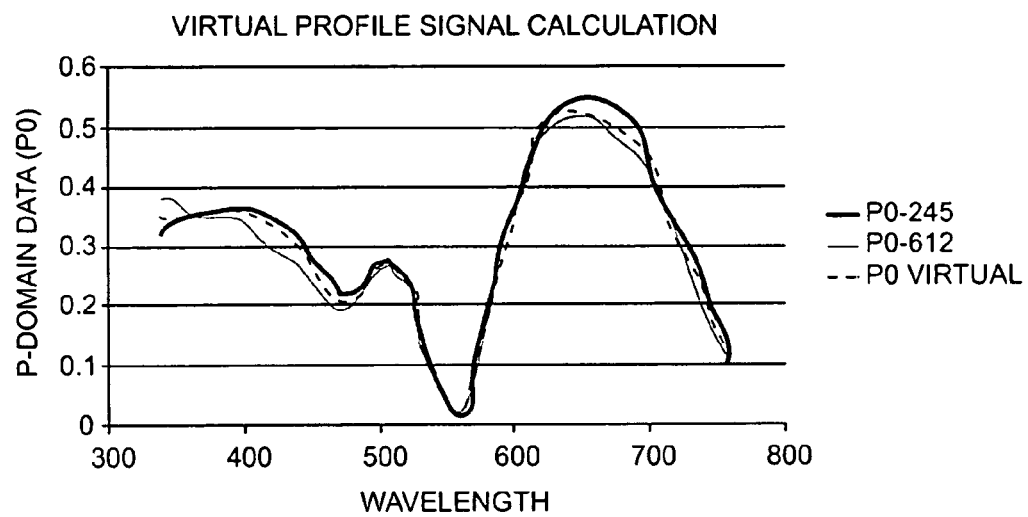
FIG. 4B illustrates a graph of virtual profile signal calculations in accordance with embodiments of the invention.

FIG. 4B illustrates a graph of virtual profile signal calculations in accordance with embodiments of the invention. In the illustrated graph P-Domain data (P0) is shown versus wavelength (nm). A first set of P0 data is shown for a 245 nm library, a second set of P0 data is shown for a 612 nm library, and a third set of P0 data is shown for a virtual profile signal that is calculated using the difference between the 245 nm library data and the 612 nm library data.

Figure 4C:
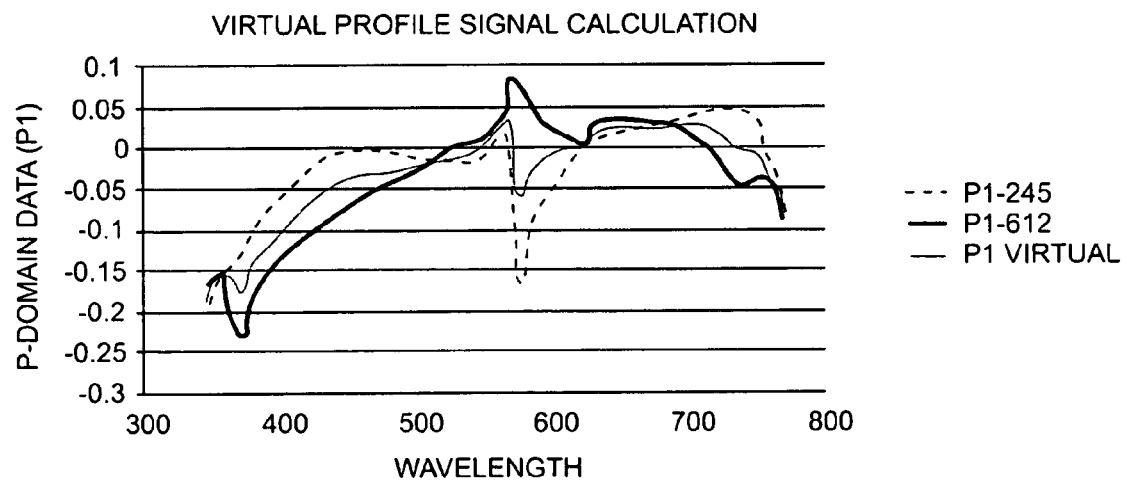
FIG. 4C illustrates a graph of additional virtual profile signal calculations in accordance with embodiments of the invention.

FIG. 4C illustrates a graph of additional virtual profile signal calculations in accordance with embodiments of the invention. In the illustrated graph P-Domain data (P1) is shown versus wavelength (nm). A first set of P1 data is shown for a 245 nm library, a second set of P1 data is shown for a 612 nm library, and a third set of P1 data is shown for a virtual profile signal that is calculated using the difference between the 245 nm library data and the 612 nm library data.

Relating these calculations back to FIG. 3C, the mapping model (matrix) 384 can be a linear model and the virtual model profile 383 can be created by scaling the "245 nm" profiles. After the virtual model profile 383 has been created a simulation can be performed, and the simulated data can be compared to the virtual profile signal data to ensure that an accurate virtual model profile has been created. In one example, the profile can include a CD (~70 nm), a resist layer (~220 nm), a BARC layer (~92 nm), an oxide layer (~3 nm), a doped poly layer (~50 nm), a poly layer (~100 nm), a gate layer (~1 nm), a SOI layer (~60 nm), and a buried oxide layer (~140 nm).

The un-refined virtual profile data can be stored in an un-refined virtual profile library. The un-refined virtual profile library can be created at an un-specified resolution, and the un-refined virtual profile library can encompass a virtual profile data space having data points with an un-specified accuracy. The data points can represent un-refined virtual profile parameters and associated un-refined virtual profile signals, and the un-refined virtual profile library can include a plurality of un-refined virtual profiles.

In 415, a query can be performed to determine if a refinement procedure is required. When a refinement procedure is required, procedure 400 can branch to 420, and when a refinement procedure is not required, procedure 400 can branch to 425.

In 420, a refinement procedure can be performed. The refinement procedure can include a series of steps designed to determine refined virtual profile parameters using data associated with the signals, data associated with the selected profiles, and other data from and/or derived from the profile data spaces.

The refined data can be stored in a refined virtual profile library. The refined virtual profile library can be created at a specified resolution, and the refined virtual profile library can encompass a refined virtual profile data space having data points with a specified accuracy. The data points can represent refined virtual profile parameters and associated refined virtual profile signals, and the refined virtual profile library can include a plurality of refined virtual profiles, An accuracy value for the data points of the refined virtual profile library can be specified and/or verified. In addition, an accuracy value for the data points of the un-refined virtual profile library can be specified and/or verified. The refined virtual profile library can be created at a specified resolution. Tolerances and/or limits can be established for the refined and/or unrefined virtual profile parameters and for the associated virtual profile signals.

A refined resolution can be calculated for the data points in the refined virtual profile data space, and the refined resolution can be designed to ensure that the specified accuracy value exists between the data points in the refined virtual profile data space, and the data points of the refined virtual profile data space can be created using the calculated refined resolution.

Before, during, and/or after a refinement procedure is performed one or more sensitivity matrices can be calculated, the sensitivity matrix being a measure of change of the signal induced by a change in the profile parameter. A sensitivity matrix can be used to determine a maximum refined resolution for each virtual profile parameter.

In 425, a query can be performed to determine if a virtual profile library is required to measure an integrated circuit structure. For example, a virtual profile library may be required when an existing library does not exist for the integrated circuit structure being examined. When a virtual profile library is required to measure an integrated circuit structure, procedure 400 can branch to 430, and when virtual profile library is not required to measure an integrated circuit structure, procedure 400 can branch to 435.

In 430, a virtual profile library can be used to measure and/or identify an integrated circuit structure. The measurement and/or identification procedure can include a series of steps designed to determine a virtual profile shape, virtual profile signal, and virtual profile parameters to identify a structure, such as an integrated circuit structure.

In some cases, reference and/or test structures can be fabricated during semiconductor processing and can be used to create, refine, and/or use a virtual profile library. In other cases, a virtual profile library can be used to identify an unknown structure. For example, a structure may not exist in a currently developed library and a virtual profile library may be used to extend the measurement and identification techniques into previously unused data spaces.

One exemplary method of using a virtual profile library to determine the profile of an integrated circuit structure can include measuring a signal off a structure with a metrology device. The measurement generates a measured signal. In a first comparison step, the measured signal can be compared to a plurality of signals in a first library, and the first comparison step can be stopped if a first matching criteria is met. In a second comparison step, the measured signal can be compared to a plurality of signals in a second library, and the second comparison step can be stopped if a second matching criteria is met. Alternatively, a different number (1-N) of libraries may be used. The libraries can include real profile data and/or virtual profile data.

When at least one matching criteria is not met, a virtual profile data space can be determined, and the virtual profile data space can be determined using differences between a profile data space associated with the first library and a profile data space associated with the second library. Alternatively, adjustment matrices may be determined and used with existing data spaces to determine a virtual profile data space.

Next, a virtual profile signal that is part of the virtual profile data space can be determined, and a virtual profile shape and/or virtual profile parameters can be determined based on the virtual profile signal. In other embodiments, a virtual profile shape that is part of the virtual profile data space can be determined, and a virtual profile signal and/or virtual profile parameters can be determined based on the virtual profile shape.

A difference can be calculated using the measured signal and the virtual profile signal, and the difference can be compared to a virtual profile library creation criteria. Alternatively, the difference can be determined using a measure profile shape and a virtual profile shape. It should be understood that when differences are discussed herein the differences can be scalars, vectors, matrices, and/or tensors. Then, either the structure can be identified using the virtual profile data associated with the virtual profile signal and/or virtual profile shape if the virtual profile library creation criteria is met, or a corrective action can be applied if the virtual profile library creation criteria is not met.

In the various examples discussed herein, applying a corrective action can include determining a new virtual profile signal, creating a new virtual profile signal, determining a new virtual profile shape, creating a new virtual profile shape, selecting a different library, creating a new virtual profile library, using a different virtual profile library creation criteria, using different wavelengths, performing a refinement procedure, performing an accuracy improvement procedure, performing a sensitivity analysis, performing a clustering procedure, performing a regression procedure, performing an optimization procedure, performing a simulation procedure, or using different metrology data, or a combination thereof.

In some cases, a new virtual profile shape and/or new virtual profile signal can be determined, selected, and/or created using one or more optimization techniques. Alternatively, an optimization technique may not be required.

A new difference can be calculated using the measured signal and the new virtual profile signal, and the difference can be compared to a virtual profile library creation criteria. Alternatively, the difference can be determined using a measure profile shape and a new virtual profile shape. It should be understood that when differences are discussed herein the differences can be scalars, vectors, matrices, and/or tensors. Then, either the structure can be identified using the new virtual profile data associated with the new virtual profile signal and/or new virtual profile shape if the virtual profile library creation criteria is met, or the procedure can be stopped if the virtual profile library creation criteria is not met.

A new virtual profile signal and/or new virtual profile shape can be determined using a new difference calculated using data in the first library and data in the second library. Alternatively, a new virtual profile signal and/or new virtual profile shape may be determined using a new data in a library and an adjustment matrix.

When an optimization technique is used, a global optimization technique and/or a local optimization technique can be used.

A virtual profile library creation criteria can include goodness of fit values and limits for virtual profile signals, virtual profile shapes, and/or virtual profile parameters.

In the various embodiments discussed herein, the virtual profile library data can be created, selected, determined, refined, compared, simulated, stored, and/or used in real time to minimize storage requirements and minimize processing times. Alternatively, dynamic processing may not be required.

When virtual profile library data is created, selected, determined, refined, compared, simulated, stored, and/or used, accuracy values and limits can be determined for the virtual profile library data. The accuracy values and limits can be established for virtual profile signals, virtual profile shapes, and/or virtual profile parameters. In addition, accuracy values and limits can be established for unrefined data, refined data, structure data, measured data, simulated data, calculated data, reference data, historical data, and/or creation criteria data.

A refinement procedure can be performed, if an accuracy value does not meet the accuracy limits. Accuracy testing can be performed using operational limits, warning limits, and/or error limits. For example, warning messages can be sent when operational limits are exceeded, and error messages can be sent when warning limits are exceeded.

Still referring to FIG. 4, in some embodiments, a linear relationship can exist between two libraries and one or more linear relationships can be used during a virtual profile creation process to create values for the virtual profile shape, the virtual profile parameters and virtual profile signals. In other embodiments, a non-linear relationship can exist between two libraries and one or more non-linear relationships can be used during a virtual profile creation process to create values for the virtual profile shape, the virtual profile parameters, and virtual profile signals.

For example, the extent of linearity and/or non-linearity between the data points in the two libraries can be examined and/or controlled in order to ensure consistent and repeatable results from refinement procedures used to determine the more accurate virtual profile parameters and spectrum. For a given variable, the extent of non-linearity between the two libraries may be measured as the deviation of the calculated number versus the value of the same variable if the relationship of the variables is linear. The extent of non-linearity can be expressed as the difference between the calculated change of the profile parameters from the actual change of the profile parameters.

The invention also ensures that an accurate virtual profile library is created by utilizing refined virtual profile resolutions for each refined virtual profile parameter used to create the refined virtual profile library. As will also be described with examples below, refined virtual profile resolutions are the maximum value of the profile parameter resolutions that can be used to create a refined virtual profile library. The refined virtual profile library can be created with the specified accuracy limits for the virtual profile shapes, the virtual profile parameters, and the virtual profile signals.

For example, for a set of virtual profile parameters consisting of CD width and height, the accuracy values specified for a fabrication run may be 1.5 nm and 2 nm respectively for CD width and for height of the IC structure, i.e., the structure may vary by these amounts without impacting the design attributes of the structure. One exemplary embodiment calculates the maximum resolution for the CD width and height when creating the virtual profile library such that the error of calculated virtual profile parameters do not exceed for example 1.5 nm and 2 nm, respectively.

Referring to FIG. 4, the difference between the two libraries can be examined to determine the amount of linearity and/or non-linearity for each unrefined virtual profile parameter when an un-refined virtual profile library is established. As discussed above, one embodiment utilizes the concept of establishing an accuracy value for each refined virtual profile parameter of a refined virtual profile library for establishing a refined (more accurate) virtual profile library. Accuracy limits may be the maximum deviation from a structure profile parameter specification without altering the design attributes of the device or circuit. Alternatively, accuracy limits may be those set by users of the IC structures and wafers based on their requirements.

One method of creating a virtual profile library includes creating a reference structure on a semiconductor wafer measuring a signal off the reference structure with a metrology device. The measurement generates a reference signal. The reference signal is compared to a plurality of signals in a first library. If a matching condition cannot be found, then the reference signal is compared to a plurality of signals in a second library. If a matching condition cannot be found, then a virtual profile data space is created. The virtual profile data space can be created using differences between a profile data space associated with the first library and a profile data space associated with the second library. The virtual profile data space being associated with the virtual profile library. Then, a virtual profile signal can be created in the virtual profile data space, and a virtual profile shape and/or virtual profile parameters can be determined based on the virtual profile signal. Next, a difference between the reference signal and the created virtual profile signal can be determined, and the difference can be compared to a virtual profile library creation criteria. Then, either the created virtual profile signal and the virtual profile data associated with the created virtual profile signal can be stored if the virtual profile library creation criteria is met, or a corrective action can be applied if the virtual profile library creation criteria is not met.

A virtual profile signal can be created using a difference between a signal in the first library and a signal in the second library. Alternatively, a virtual profile signal may be created using a signal in a library and an adjustment matrix.

In one example, applying a corrective action can include a number of steps such as creating a new virtual profile signal of the virtual profile data space; a new virtual profile shape and/or new virtual profile parameters can be created based on the new virtual profile signal; and an optimization technique is performed to select the new virtual profile signal. Then, calculating a difference between the reference signal and the new virtual profile signal, and comparing the difference to a virtual profile library creation criteria. Then, either the newly created virtual profile signal and the virtual profile data associated with the newly created virtual profile signal can be stored if the virtual profile library creation criteria is met, or the creating, the calculating, and the comparing steps may be stopped, if the virtual profile library creation criteria is not met.

A new virtual profile signal can be created using a new difference between a signal in the first library and a signal in the second library. Alternatively, a new virtual profile signal may be created using a new signal in a library and an adjustment matrix.

When an optimization technique is used, a global optimization technique and/or a local optimization technique can be used.

A virtual profile library creation criteria can include a goodness of fit value.

In various embodiments, the virtual profile signals and/or virtual profile shapes can be created in real time using differences between the signals in the first library and the signals in the second library, and/or using differences between profile shapes in the first library and profile shapes in the second library. Alternatively, the virtual profile signal may be created using a plurality of virtual profile signals in the virtual profile library.

When signal differences are calculated, different bandwidths and/or different wavelengths can be used. For example, when a difference between a reference signal and the created virtual profile signal is determined, a plurality of wavelengths can be used and the plurality of wavelengths can include wavelengths from approximately 100 nm to approximately 1000 nm.

In addition, the virtual profile data space can be segmented into smaller pieces to facilitate the library creation process. A clustering technique can be used and a first cluster space can be created within the virtual profile data space, and the first cluster space can be created using differences between a first cluster associated with the first library and a second cluster associated with the second library. A virtual profile signal can be created and/or selected within the first cluster space, and the first cluster space can contain the reference signal and data points proximate to the data point associated with the created virtual profile signal. Next, a difference between the reference signal and the created first virtual profile signal can be calculated, and the difference can be compared to a virtual profile cluster creation criteria. Then, either the data point associated with the created virtual profile signal can be stored in the virtual library as a member of the first cluster space if the virtual profile cluster creation criteria is met, or applying a corrective action if the virtual profile cluster creation criteria is not met.

In a clustering example, applying a corrective action can include a number of steps such as creating a new virtual profile signal within the first cluster space; a new virtual profile shape and/or new virtual profile parameters can be created based on the new virtual profile signal; and an optimization technique is performed to select the new virtual profile signal. The first cluster space can contain the reference signal and data points proximate to the data point associated with the newly created virtual profile signal. Then, a new difference between the reference signal and the new virtual profile signal can be calculated, and the new difference can be compared to a virtual profile library creation criteria. Then, either the data point associated with the newly created virtual profile signal in the virtual library can be stored as a member of the first cluster space if the virtual profile cluster creation criteria is met, or the creating, the calculating, and the comparing steps may be stopped, if the virtual profile cluster creation criteria is not met.

In another example, a virtual profile shape can be created and/or selected within the first cluster space. The first cluster space can contain the reference signal and data points proximate to the data point associated with the created virtual profile shape. A simulation can be performed that simulates a signal off a structure with virtual profile parameters corresponding to the created virtual profile. Next, a difference between the reference signal and the simulated signal can be calculated, and compared to a virtual profile cluster creation criteria. Then, either the data point associated with the created virtual profile can be stored in the virtual library as a member of the first cluster space if the virtual profile cluster creation criteria is met, or another a corrective action can be performed if the virtual profile cluster creation criteria is not met.

When a corrective action is performed, new virtual profiles can be selected or created within the first cluster space. In addition, the new virtual profiles can be examined, and some of the new virtual profiles can be stored.

In some embodiments, a reference profile can be determined that is associated with the reference signal. Differences between the reference profile and the created virtual profile can be calculated and compared to a virtual profile library creation criteria. The created and/or simulated virtual profile and the virtual profile data associated with the created and/or simulated virtual profile can be stored if the virtual profile library creation criteria is met, or a corrective action can be applied if the virtual profile library creation criteria is not met.

The corrective action can include creating and/or selecting new virtual profiles in the virtual profile data space, and a new virtual profile signal and/or new virtual profile parameters can be created based on the new virtual profile. The newly created and/or newly simulated virtual profile and the virtual profile data associated with the newly created and/or newly simulated virtual profile can be stored if the virtual profile library creation criteria is met, or the corrective action can be stopped if the virtual profile library creation criteria is not met.

In other embodiments, unrefined and/or refined virtual profile shapes, virtual profile signals and/or virtual profile parameters can be created before, during, and/or after a virtual profile library is created. A virtual profile sensitivity matrix can be created and/or created. The virtual profile sensitivity matrix can be a measure of the change of a virtual profile signal induced by a change of a virtual profile parameter. For example, a virtual profile sensitivity matrix can be determined using a sensitivity matrix associated with the first library, or a sensitivity matrix associated with the second library, or a combination thereof. In addition, an adjustment value can be determined for the virtual profile parameters using the computed sensitivity matrix, and the virtual profile parameters can be created by adding the adjustment value of the virtual profile parameters to corresponding profile parameters of a best estimate data point in the first library, or a best estimate data point in the second library, or a best estimate data point outside the libraries.

Furthermore, an adjustment matrix can be computed, and the adjustment matrix can include an adjustment value for at least one virtual profile parameter, and each adjustment value can be determined using a profile parameter associated with a profile of the first library, or a profile parameter associated with a profile of the second library, or a combination thereof. Alternatively, an adjustment value may be determined using a diffraction signal associated with a profile of the first library, or a diffraction signal associated with a profile of the second library, or a combination thereof The virtual profile can be created by using the adjustment matrix and the profile parameters associated with the first library, or the profile parameters associated with the second library, or profile parameters associated with a data point outside the libraries, and the virtual profile signal can be created by simulating a signal off a structure with virtual profile parameters corresponding to the created virtual profile.

In additional embodiments, virtual profile libraries and library instances can be created using best matches and/or best estimates. A best estimate of the reference signal can be created in the virtual profile data space, and the best estimate can be created using differences between a profile data space associated with the first library and a profile data space associated with the second library. The virtual profile data space can have data points with specified accuracy values, the virtual profile parameters can provide a characterization of a profile of an integrated circuit structure, and the best estimate/ match can be a data point of the virtual profile data space with a signal closest to the reference signal.

In various embodiments, a polyhedron can be created or selected in the virtual profile data space. Alternatively, polyhedrons may be established in non-virtual libraries. A polyhedron can be determined using a best estimate or best match data point and can have corners corresponding to selected profile parameter data points in the virtual profile data space that are proximate to the best estimate or best match data point. Next, a total cost function associated with the polyhedron can be minimized, and the total cost function can include a cost function of the signals corresponding to the selected profile parameter data points relative to the reference signal and a cost function of the best estimate signal relative to the reference signal. When the minimization is successful, the created virtual profile data can be stored. The polyhedron can have at least one corner associated with each virtual profile parameter.

The total cost function can be minimized by selecting a set of weighting vectors; each weighting vector can have vector elements, and each vector element can be associated with the virtual profile signal corresponding to a selected data point. Next, a total cost function can be calculated for each weighting vector of the set of weighting vectors, and the weighting vector that yields the minimum total cost function can be selected. Then, the virtual profile data can be created or refined using the weighting vector associated with the minimum total cost function.

In addition, other methods can be used when creating, refining, and/or using a virtual profile library. Accuracy value can be created and/or determined for the virtual profile data in a virtual profile library. For example, accuracy values can be determined for created and/or selected virtual profile signals and/or virtual profile shapes. The accuracy value can be compared to accuracy limits, and a refinement procedure can be performed if the accuracy value does not meet the accuracy limits.

A refinement procedure can be performed to create refined virtual profile parameters that correspond to virtual profile signals and/or virtual profile shapes. The virtual profile signals and/or virtual profile shapes can be determined using reference values, measured values, simulated values, historical values, library based differences, or library based equations. The refined data can be verified using a refined virtual profile creation criteria. The refined virtual profile creation criteria can include a goodness of fit value.

In addition, unrefined accuracy limits can be established and used to create, refine, and/or use an unrefined and/or refined virtual profile library. For example, when virtual profile data does not meet refined accuracy limits that data may be stored in an unrefined virtual profile library. In addition, an unrefined accuracy value can be established for an unrefined virtual profile, an unrefined virtual profile signal, or a set of unrefined virtual profile parameters, or a combination thereof.

The metrology devices used to create, refine, and/or use an unrefined and/or refined virtual profile library can include an optical metrology device, an electron metrology device, an electrical metrology device or a mechanical metrology device.

The structures established and used to create, refine, and/or use an unrefined and/or refined virtual profile library can be verified using a CD-scanning electron microscope (CD-SEM), a transmission electron microscope (TEM), and/or a focused ion beam (FIB) devices.

The refinement procedure can utilize bilinear refinement, Lagrange refinement, Cubic Spline refinement, Aitken refinement, weighted average refinement, multi-quadratic refinement, bi-cubic refinement, Turran refinement, wavelet refinement, Bessel's refinement, Everett refinement, finite-difference refinement, Gauss refinement, Hermite refinement, Newton's divided difference refinement, osculating refinement, or Thiele's refinement algorithm, or a combination thereof.

In still other embodiments, methods of expanding a virtual profile library can be established and used. A signal off a structure can be determined using a metrology device, and the measurement can generate a measured signal and/or measured profile. Next, a difference between the measured signal and a refined virtual profile signal in a refined virtual profile library can be calculated, and the difference can be compared to an unrefined and/or refined virtual profile library creation criteria. Then, either the structure can be identified using unrefined or refined virtual profile data associated with the unrefined or refined virtual profile signal and/or virtual profile shape, if the unrefined or refined virtual profile library creation criteria is met, or applying a first corrective action if the unrefined or refined virtual profile library creation criteria is not met.

When applying a first corrective action, a second difference can be calculated using the measured signal and an unrefined virtual profile signal in an unrefined virtual profile library, and the second difference can be compared to an unrefined virtual profile library creation criteria. Then, either the structure can be identified using the unrefined virtual profile data associated with the unrefined virtual profile signal if the unrefined virtual profile library creation criteria is met, or a second corrective action can be applied if the unrefined virtual profile library creation criteria is not met.

When applying the second corrective action, a new virtual profile signal can be created in the virtual profile data space, and a new virtual profile shape and/or new virtual profile parameters can be created based on the new virtual profile signal. A third difference can be calculated using the measured signal and the new created virtual profile signal, the third difference can be compared to an unrefined virtual profile library creation criteria. Then, either the new created virtual profile signal and the virtual profile data associated with the created virtual profile signal can be stored in an unrefined virtual profile library, if the virtual profile library creation criteria is met, or a third corrective action can be applied if the unrefined virtual profile library creation criteria is not met.

When applying the third corrective action, an accuracy value can be determined for the new created virtual profile signal, and the accuracy value can be compared against accuracy limits, and a refinement procedure can be performed if the accuracy value does not meet the accuracy limits.

In exemplary embodiments, the following exemplary set of steps can be used for creating, refining, and/or using a virtual profile library.

In step 1, given a set of un-refined virtual profile parameters, UVP, for an un-refined virtual profile library, where;

UVP=($uvp_1$, $uvp_2$, ... $uvp_K$).

One can establish an un-refined resolution and/or accuracy value of each un-refined virtual profile parameter, and express it as a vector:

Un-refined Resolution UR=($UR_1$, $UR_2$, ... $UR_K$), where K is the number of profile parameter dimensions.

When considering a refined virtual profile library, a set of refined virtual profile parameters, RVP, can be used where:

RVP=($rvp_1$, $rvp_2$, ... $rvp_K$).

One can establish a refined resolution and/or accuracy value for each refined virtual profile parameter, and express it as a vector:

Refined Resolution RR=($RR_1$, $RR_2$, ... $RR_K$), where K is the number of profile parameter dimensions.

In step 2, one can select a set of un-refined virtual profile parameters, $UVP_{SET0}$, as follows:

$UVP_{SET0}$=($uvp_1$, ... $uvp_{L-1}$, $uvp_L$, $uvp_{L+1}$, ... $uvp_K$), where L is any un-refined virtual profile parameter from 1 to K.

In step 3, one can simulate a diffracted spectrum off a structure using unrefined virtual profile parameters. An unrefined virtual profile signal (un-refined simulated signal) can be generated for each un-refined virtual profile in an un-refined virtual profile library. For example, a first diffracted spectrum off an un-refined virtual profile can be simulated using the selected first set of unrefined virtual profile parameters $UVP_{SET0}$, and a first unrefined simulated diffraction spectrum $S^{uvp0}$ can be generated.

In step 4, an incrementing process can be performed. For example, one un-refined virtual profile parameter $uvp_L$ of a selected set, $UVP_{SET0}$, can be selected at a time, and the selected un-refined virtual profile parameter $uvp_L$ can be incremented by a small amount $\beta_L$, designating the new set of un-refined virtual profile parameters $UVP_{INCR}$. For example, $uvp_L$ may be the CD width and CD width may range from 100 to 300 nm while the increment $\beta_L$ may be 1 or 2 nm. However, the increment for the profile parameter may vary depending on experience from previous library creation processes for the particular fabrication run.

In step 5, a new unrefined virtual profile signal (new un-refined simulated signal) can be determined each time the un-refined virtual profile is incremented. For example, one can simulate the diffracted spectrum off an IC structure with the unrefined virtual profile parameter set $UVP_{INCR}$, and thereby generating an unrefined diffracted spectrum $S^L$.

In step 6, a sensitivity analysis step can be performed. For example, one can calculate the sensitivity of change of spectrum, $\delta S$, corresponding to the change in an unrefined virtual profile parameter, $\delta uvp$:

$$\frac{\delta S^L}{\delta uvp} = \frac{(S^L - S^{uvp0})}{\beta_L},$$

where $S^L$ is a column vector of length N, and N is the number of spectrum data points for each measurement performed with the metrology device.

In step 7, one of the other unrefined virtual profile parameters can be changed by a small increment $\alpha$ (0.2 nm). The small increment $\alpha$ can be application dependent and generally based on empirical data, and the small increment $\alpha$ is typically a fraction of the profile increment $\beta_L$.

In step 8, one can simulate a new diffracted spectrum, $S^i$ using the changed un-refined virtual profile parameter while the rest of the un-refined virtual profile parameters are held constant, and this step can be repeated for all the other unrefined virtual profile parameters. For a profile parameter i, the general form of the equation is:

$$\frac{\delta S^i}{\delta uvp_i} = \frac{(S^i - S^{uvp0})}{\alpha},$$

where $\delta S^i$ is the change of the unrefined diffracted spectrum induced by the change in an unrefined virtual profile parameter $\delta uvp_i$. Each of the $S^i$ is a column vector of length N, and N is the number of spectrum data points for each measurement performed with the metrology device.

In step 9, one can compute the sensitivity matrix J by substituting the values calculated in foregoing steps:

$$J = \left[ \frac{\delta S^1}{\delta uvp_1}, \frac{\delta S^2}{\delta uvp_2}, \ldots \frac{\delta S^K}{\delta uvp_K} \right],$$

where $S^1$ is a column vector of length N, $S^2$ is a column vector of length N, etc., and N is the number of spectrum data points for each measurement performed with the metrology device.

In step 10, one can simulate the diffracted spectrum using the set of profile parameters:

UVP=($uvp_1$, ... $uvp_{L-1}$, ($uvp_L+\beta_L/2$), $uvp_{L+1}$, $uvp_K$), generating diffracted spectrum $S^{UVP}$.

In step 11, one can use the sensitivity matrix J calculated above and the new $\delta S$ value calculated using the equation $\delta S = S^{UVP} - S^{uvp0}$, calculate $\delta UVP$ as follows:

$$\delta UVP = (J^T J)^{-1} J^T \delta S,$$

yielding:

$$\delta UVP = (b_1, \ldots b_{L-1}, b_L, b_{L+1}, \ldots b_K),$$

where $b_1$ is the calculated value of the change in the first unrefined virtual profile parameter $uvp_1$, $b_L$ is the calculated value of change in the $L^{th}$ unrefined virtual profile parameter $uvp_L$, and so on.

Next, the accuracy of the virtual profile library created with the refined resolution or resolutions calculated using the above steps can be tested to see if the data in the virtual profile library meets the specified accuracy criteria. If the accuracy test requirement is not met, a corrective action can be applied.

An example of performing the accuracy test and applying a corrective action is described below for the technique using threshold deviations:

In step 12, the calculated $\delta UVP$ can be compared to the ideal values of $\delta UVP$ and the absolute values of the differences between the ideal values of $\delta UVP$ and calculated values of $\delta UVP$ can be tested to see if these are equal to or less than the accuracy limits. Ideal values for the profile parameter $\delta vp$ are zero for parameters other than the $L^{th}$ unrefined virtual profile parameter, $uvp_L$ and one half of $\beta_L$ for the $L^{th}$ unrefined virtual profile parameter, $uvp_L$. Expressed in equation form, the accuracy test can be as follows:

Compare $|0-b_1| \leq T_1 \ldots |\beta_L/2 - b_L| \leq T_L \ldots$ and $|0-b_K| \leq T_K$.

If the comparisons in above equations are "True", i.e., the maximum accuracy limit for virtual profile parameter vpL has not been exceeded, then increment the value of $\beta_L$. For example, $\beta_L$ may be incremented by 1 nm. Repeat Steps 5 through 12 until the comparison is "False" and take the last value of $\beta_L$ where the comparison was "True", this value of $\beta_L$ being the virtual profile accuracy limit for a refined virtual profile parameter rvpL.

In step 13, steps 1 through 12 can be repeated for the rest of the virtual profile parameters and the refined virtual profile data can be saved. The refined virtual profile library can be created for the ranges of the profile parameters that meet the accuracy limits for the refined virtual profiles. For example, the CD width may have a range of 100 to 200 nm and the refined virtual profile accuracy limit of the CD width that meets the specified accuracy limits may be 4 nm.

Another embodiment for determining virtual profile accuracy limits of the virtual profile parameters recognizes that in order for the accuracy requirement to be satisfied, more than one un-refined and/or refined virtual profile accuracy limit may be needed. This approach recognizes that over the entire range of the virtual profile parameters, different accuracies may be applied. The entire range of the virtual profile parameters can be partitioned into several partitions. Within each partition, virtual profile parameter accuracies can be determined in a similar manner as described above. Instead of using one set of virtual profile accuracies to create a profile library, a set of virtual profile accuracy values specific to the virtual profile parameter partition can be used. Using the previous example, the CD width may have a range of 100 to 300 nm and the virtual profile accuracy value of the CD width may be 3 nm for the first partition 100-200 nm, 2.5 nm for the second partition of 201-250 nm, and 1.8 nm for the third partition 251-300 nm. Alternatively, other techniques or algorithms may be employed to perform a refinement procedure or ensure that the set of virtual profile data points in a refined virtual profile library meet accuracy requirements.

FIG. 5A through FIG. 11 use optical metrology to illustrate and describe the concepts and principles used in the present invention. As mentioned above, the concepts and principles described also apply to other metrology systems such as electron, electric, and mechanical metrology systems.

Figure 5A:
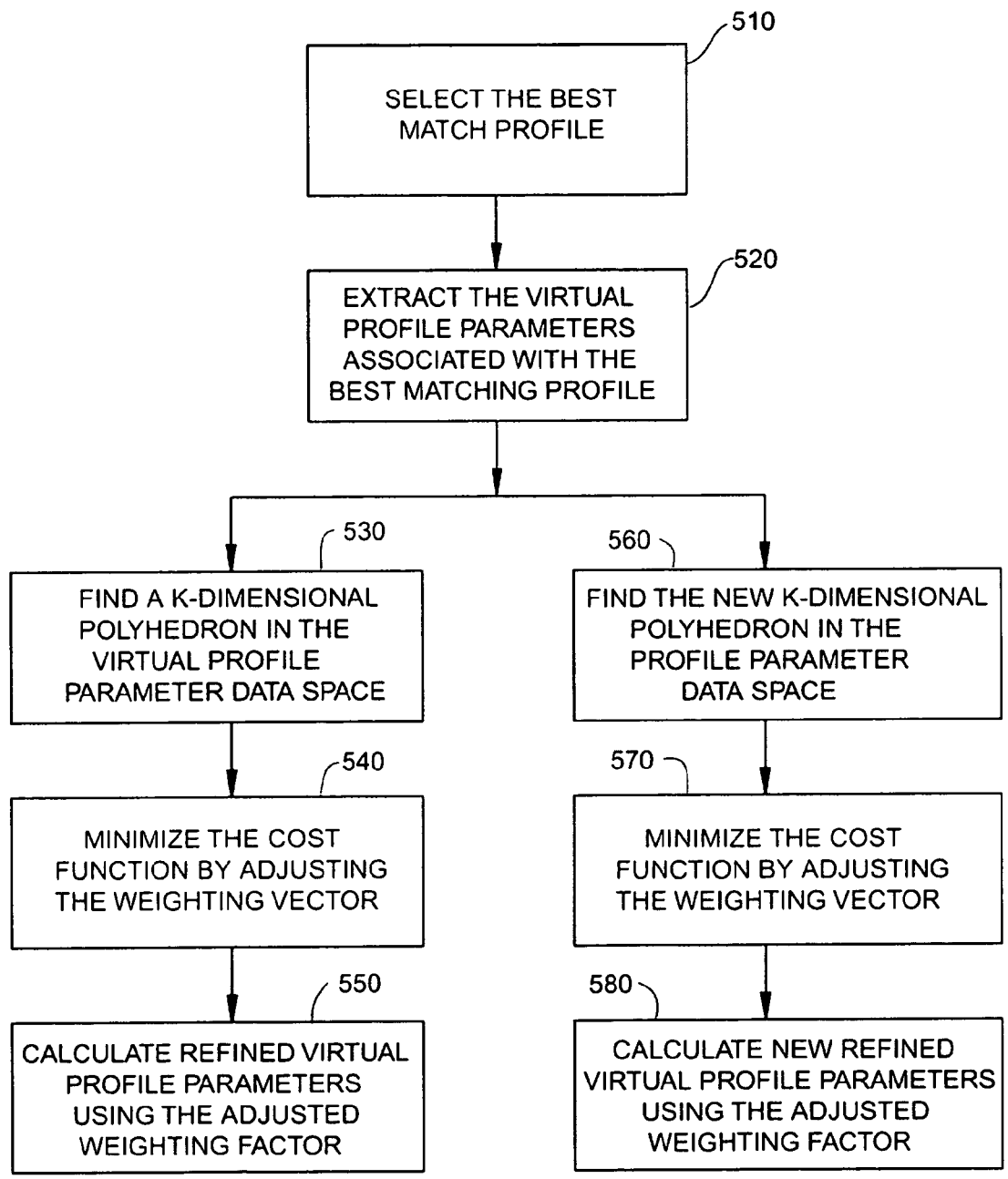
FIG. 5A illustrates a flow chart of a procedure for refining virtual profile library data using cost functions in accordance with embodiments of the invention.

FIG. 5A illustrates a flow chart of a procedure for creating and/or refining virtual profile library data using cost functions in accordance with embodiments of the invention. In the illustrated embodiment, the virtual profile refinement procedure is performed by minimizing the cost function of selected spectra data points in a virtual profile library compared to the measured diffracted spectra and utilizing a weighting vector. The virtual profile refinement process can be performed after creating a virtual library with a specified and/or unspecified accuracy limits. The measured diffracted spectrum, $S^M$, off a reference/test structure can be compared to the spectra in the virtual profile library and the best match spectrum, $S^0$, in the virtual profile library can be selected 510. The virtual profile parameters associated with the best match library spectrum can be extracted 520. The data point representing the virtual profile parameters associated with the best match library spectrum can be designated as $vp^0$.

The total cost function of selected spectra data points in the virtual profile library compared to the measured diffracted spectra is calculated. The total cost function is minimized utilizing a weighting factor. Selection of spectra data points varies according to the embodiment. In one exemplary embodiment, a K-dimensional polyhedron is selected in the virtual data space of virtual profile parameters, the polyhedron can be configured to contain the virtual profile parameters of the best match library spectrum and can be configured such that the corners or vertices of the polyhedron correspond to the selected virtual profile parameter data points 530. As previously defined, a data point refers a set of profile parameters and the associated spectrum, while a data space is a collection of data points, and a library can comprise a plurality of data spaces. Selection of the virtual profile parameter data points for the K-dimensional polyhedron can be done by selecting neighboring values of the virtual profile parameters associated with the best match virtual profile library spectrum, and the neighboring values can be chosen in a direction that yields a smaller spectrum variance between the measured spectrum and the spectrum associated with the data point, as illustrated in FIG. 5B.

Figure 5B:
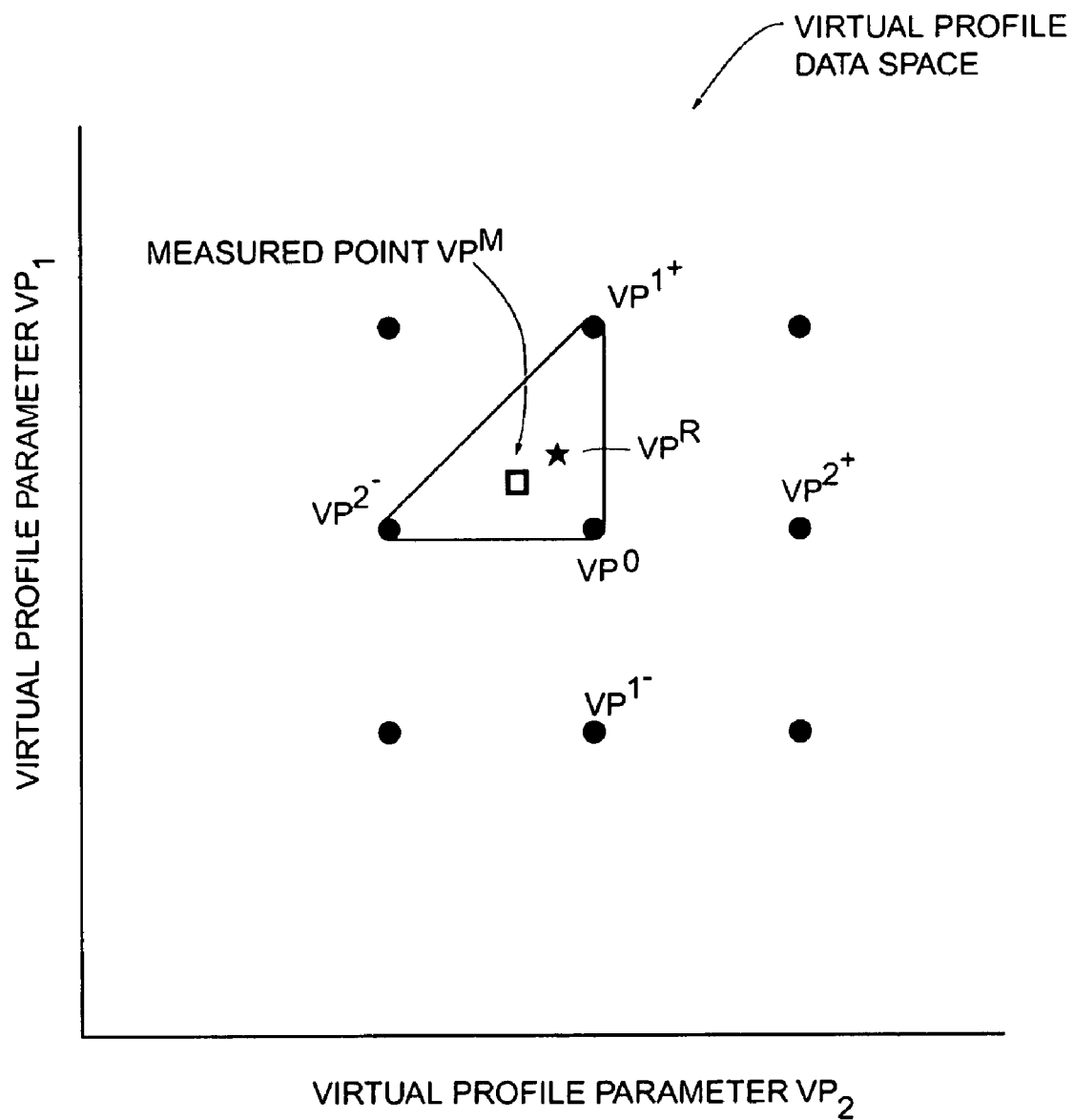
FIG. 5B illustrates an exemplary view of a virtual profile data space in accordance with embodiments of the invention.

Referring to FIG. 5B, assume a simple profile of the reference/test structure being a rectangle with two profile parameters used, namely, CD width $vp_1$, and height $vp_2$, and $vp^R$ is the refined or calculated parameter data point whereas $vp^M$ is the actual parameter data point corresponding to the measured spectrum $S^M$. The best match profile parameter data point, $vp^0$, associated with the best match spectrum, $S^0$ (not shown), is the starting point for selecting the other profile parameter data points. In the case of profile parameter $vp_1$ (Y-axis value), the neighboring values of $vp^0$ are $vp^{1+}$ in the positive direction and $vp^{1-}$ in the negative direction of $vp_1$. The associated spectra (not shown) for $vp^{1+}$ and $vp^{1-}$ are $S^{1+}$ and $S^{1-}$ respectively. If the cost function of $S^{1+}$ compared to the measured spectrum $S^M$ versus the cost function of $S^{1-}$ compared to the measured spectrum $S^M$ is smaller, then $vp^{1+}$ is selected as the data point for the CD width $vp_1$, else, $vp^{1-}$ is selected. A similar analysis is made for profile parameter $vp_2$ and for this example, profile parameter data point $vp^{2-}$ is selected for the height $vp_2$. In the present example, the polyhedron is the triangular space that includes the measured parameter data point $vp^M$ with corners $vp^0$, $vp^{1+}$, and $vp^{2-}$.

For a more complex virtual profile shapes requiring, for example, seven profile parameters, K is equal to 7, and the polyhedron with eight corners, (K+1), is a hexahedron. A similar set of steps is applied for selecting the neighboring data points of the virtual profile parameters regardless of the value of K. Although a trapezoidal profile is frequently used in the examples, the concepts and principles of the present invention are applicable to other profiles, such as non-trapezoidal profiles with top rounding, bottom footing, T-topping, undercut, with straight, concave sidewalls, or convex sidewalls and non-trapezoidal profiles with various combinations of shapes and configuration characteristics Referring now to FIG. 5A, in 540, the cost function of the best match spectrum relative to the measured diffracted spectrum and the cost function of spectra associated with the selected data points relative to the measured diffracted spectrum can be minimized by adjusting the weighting vector. The equation to minimize the cost function for one embodiment is:

$$\text{MIN}_W C(W),$$

such that:

$$\sum_{i=1}^{K} W_i = 1 \text{ and } W_i \geq 0,$$

and where:

$$C(W) = \|[S^0, S^1, \ldots S^K]_{N(K+1)} W_{K+1} - S^M\|.$$

C is the total cost function. K is the number of profile parameter dimensions. N is the number of spectrum data points for each measurement performed with the metrology device. S is the diffracted spectrum. $S^0$ is the best match spectrum. $S^1$ is the spectrum associated with the chosen value of the first profile parameter, and so on up to $S^K$. $S^M$ is the measured spectrum. W is the weighting vector.

The weighting vector W is given by the equation:

$$W = \begin{bmatrix} W_0 \\ W_1 \\ \vdots \\ W_K \end{bmatrix},$$

where $W_0$ is the weight for the best match data point, $W_1$ is the weight of the first virtual profile parameter data point, and so on. The norm value of any vector V where i may be 1, 2 or any integer and for a length M is given by the equation:

$$\|V\|_i \equiv \left[\sum_{K=1}^{M} |V_K|^i\right]^{1/i}$$

Optimization of the value of the weighting vector is subject to two constraints, namely, first, the sum of the weighting vectors must equal one, and second, the value of the weighting vector may be equal or greater than zero.

Referring now to FIG. 5A, in 550, the virtual profile parameters are calculated by using the weighting vector that minimizes the total cost function of the profile parameters as expressed in the equation:

$$VP^R = (VP^0, VP^1, \ldots VP^K) \begin{bmatrix} W_0 \\ W_1 \\ \vdots \\ W_K \end{bmatrix},$$

where $VP^R$ is a vector representing the virtual profile parameters. $VP^0$ is a vector representing the profile parameters of the best match spectrum. $VP^1$ and $VP^K$ are vectors representing the profile parameters of the first and $K^{th}$ corners of the polyhedron. When considering a rectangular profile, the virtual profile parameters is given by the equation:

$$VP^R = (VP^0, VP^1, VP^2) \begin{bmatrix} W_0 \\ W_1 \\ W_2 \end{bmatrix}$$

Figure 5C:
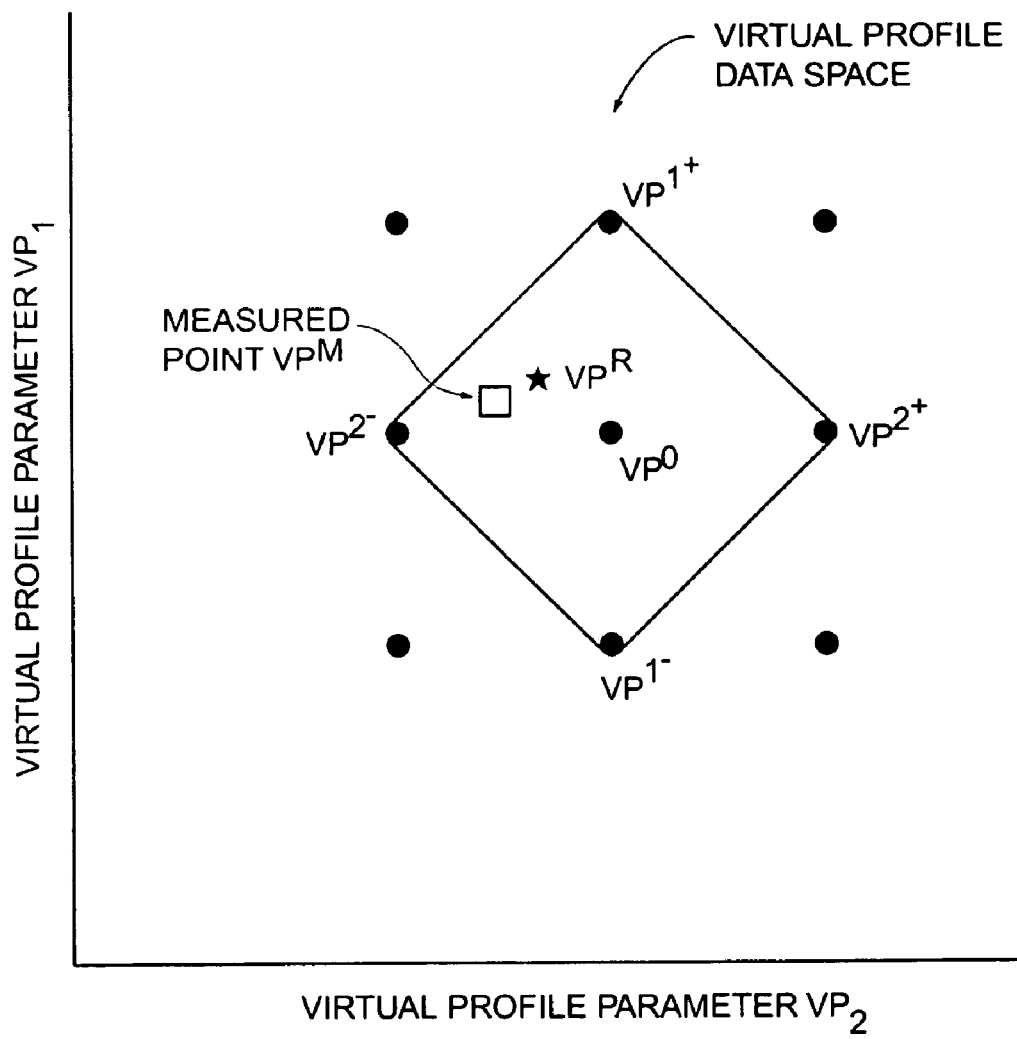
FIG. 5C illustrates another exemplary view of a virtual profile data space in accordance with embodiments of the invention.

In another embodiment, a different polyhedron with a different number of corners is used. Referring to FIG. 5A, in 560, the selection of the virtual profile parameter data points for the polyhedron corners can be done by selecting neighboring values of the profile parameters associated with the best match library spectrum. Referring to FIG. 5C, assume the rectangular structure profile of the previous example with the two profile parameters, namely, CD width, $uvp_1$, and height, $uvp_2$. Referring to FIG. 5C, $vp^R$ is the refined or calculated parameter data point whereas $vp^M$ is the actual parameter data point for the measured spectrum (not shown). The best match profile parameters point, $vp^0$, associated with the best match spectrum $S^0$ (not shown), is the starting, point for selecting the other profile parameter data points. In the case of virtual profile parameter $vp_1$ in the Y-axis, both the neighboring values $vp^{1+}$ in the positive direction and $vp^{1-}$ in the negative direction of $vp_1$ are selected. Similarly, both the neighboring $vp^{2+}$ in the positive direction and $vp^{2-}$ in the negative direction of $vp_2$ in the X-axis are selected. The polyhedron is configured to include the measured point $vp^M$ and the selected four neighboring values as corners. Regardless of the value of K, a similar set of steps is applied for selecting the neighboring data points of the virtual profile parameters. In 570, a new cost function can be determined and in 580, new virtual profile parameters can be calculated by using a new weighting vector that minimized a new total cost function.

Figure 6A:
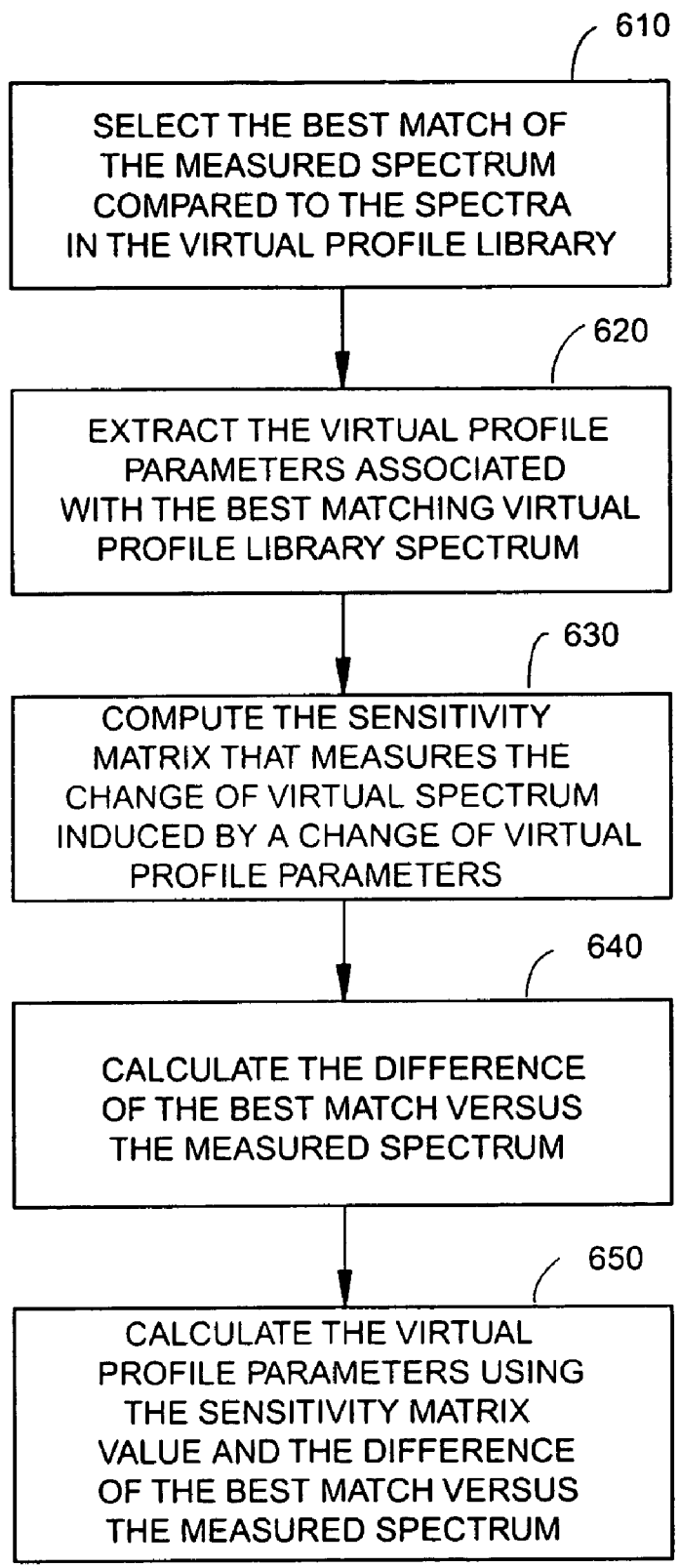
FIG. 6A is a flow chart of a procedure for creating or refining virtual profile library data using sensitivity analysis in accordance with embodiments of the invention

FIG. 6A is a flow chart of a procedure for creating and/or refining virtual profile library data using sensitivity analysis in accordance with embodiments of the invention. The virtual profile refinement process can be performed after creating an un-refined virtual profile library with known and/or unknown inaccuracies. The measured diffracted spectrum off a reference structure can be compared to the spectra in the virtual profile library and the best matching spectrum is selected 610. The virtual profile parameters associated with the best matching virtual profile library spectrum are extracted 620.

In an exemplary embodiment, a sensitivity matrix equation can be used to find the adjustment value to convert the best matching profile parameters to the virtual profile parameters. The basic equation for the sensitivity matrix J is:

$$J = \delta S / \delta VP.$$

S is the diffracted spectrum measured by an optical metrology device. δS is the change of the diffracted spectrum induced by the change of VP. VP represents the virtual profile parameters. δVP is the change of the virtual profile parameter value. K is the number of virtual profile parameter dimensions. N is the number of spectrum data points for each measurement performed with the metrology device. $S=(S_1, S_2, \ldots S_N)$, where $S_1$ the diffracted spectrum measured at measurement point 1, $S_2$ is the diffracted spectrum measured at measurement point 2, and so on. $VP=(vp_1, vp_2, \ldots vp_K)$, where $vp_1$ is the first virtual profile parameter, $vp_2$ is for the second virtual profile parameter, and so on. Expanding the sensitivity matrix equation yields:

$$J = \left[ \frac{\delta S^1}{\delta uvp_1}, \frac{\delta S^2}{\delta uvp_2}, \ldots \frac{\delta S^K}{\delta uvp_K} \right],$$

where $S^1$ is a column vector of length N, $S^2$ is a column vector of length N, etc.

The value of the sensitivity matrix J can be calculated by changing one virtual profile parameter by a small amount while keeping the others constant and calculating the incremental change in the spectrum as a result of the change in the virtual profile parameter 630. This process is repeated for all the other profile parameters, the general equation as follows:

$$J_{ij} = \frac{\delta S_i}{\delta vp_j},$$

where i is a spectrum data point for the measurement performed with the metrology device ranging from 1 to N. j is a virtual profile parameter dimension ranging from 1 to K. $J_{ij}$ is the value of the sensitivity matrix corresponding to the change in the virtual profile parameter j. $\delta S_i$ is the change of the spectrum corresponding to change of the $\delta vp_j$. $\delta S$ is the difference between the best match spectrum $S^0$ and S', where S' is the spectrum calculated using optical metrology simulation techniques for the value of the set of virtual profile parameters taking into account the incremental change to one selected virtual profile parameter. The process of calculating a spectrum using optical metrology simulation techniques is described in co-pending U.S. patent application Ser. No. 09/764,780, entitled CACHING OF INTRA-LAYER CALCULATIONS FOR RAPID RIGOROUS COUPLED-WAVE ANALYSES, by Niu, et al., filed on Jan. 25, 2001 and is incorporated herein by reference.

Figure 6B:
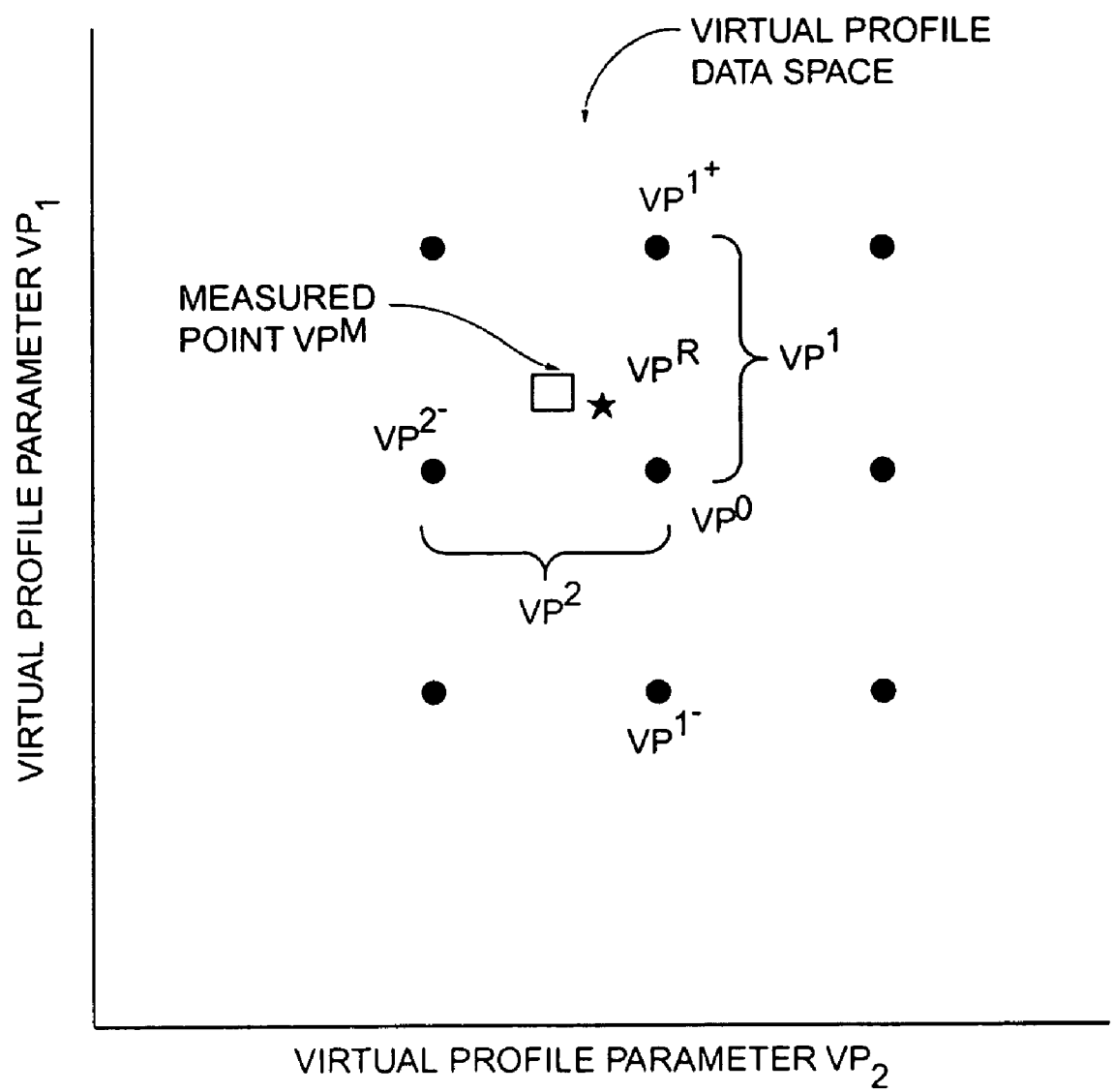
FIG. 6B is a graphical illustration of a procedure for creating or refining virtual profile library data using sensitivity analysis in accordance with embodiments of the invention.

FIG. 6B is a graphical illustration of a procedure for creating and/or refining virtual profile library data using sensitivity analysis in accordance with embodiments of the invention. Given a virtual profile library 690 assuming a structure with two virtual profile parameters, the FIG. 6B includes a graph of virtual profile parameters $vp_1$ and $vp_2$ in the Y-axis and X-axis respectively. Every data point in the graph represents a set of virtual profile parameters with corresponding diffracted spectra (not shown). For example, $VP^0$ represents the virtual profile parameters of the best match spectrum $S^0$, $vp^M$ represents the virtual profile parameters of the measured spectrum $S^M$, $vp^{1+}$ represents the virtual profile parameters of a neighboring data point in the positive direction of virtual profile parameter $vp_{-1}$ of the spectrum $S^{1+}$, $vp^{1-}$ represents the virtual profile parameters of a neighboring data point in the negative direction of virtual profile parameter $vp_1$ of the spectrum $S^{1-}$, and so on. For this example and referring to FIG. 6A, $\delta vp_1$ is the change of virtual profile parameter $vp_1$ when incremented in the positive direction and $\delta vp_2$ is the change of profile parameter $vp_2$ when incremented in negative direction. It is understood that the principles and concepts of the present invention applies to embodiments that have more than two virtual profile parameters.

In 640, the difference between the best match spectrum, $S^0$, and the measured spectrum, $S^M$, can be calculated. In 650, the virtual profile parameters, $VP^R$, can be calculated using the sensitivity matrix value and the difference between the best match spectrum and the measured spectrum.

In an exemplary embodiment where the change of S induced by a change in vp is linear, the δS and δVP can be approximated by ΔS and ΔVP respectively. Using the basic sensitivity matrix equation and substituting ΔS and ΔVP gives the equation:

$$\Delta S = J \Delta VP,$$

where:

$$\Delta S = (\Delta S_1, \Delta S_2 \ldots \Delta S_N),$$

$$\Delta VP = (\Delta vp_1, \Delta vp_2 \ldots \Delta vp_K).$$

ΔVP is calculated by using the following equation:

$$\Delta VP = (J^T J)^{-1} J^T \Delta S,$$

where J is the sensitivity matrix calculated in the previous step and ΔS is the difference between the measured spectrum and the best match library spectrum. The value of the refined profile parameters PR is given by the equation:

$$VP^R = VP^0 + \Delta VP,$$

where $VP^0$ represents the profile parameters associated with the best match spectrum and ΔVP is the adjustment value derived from the previous step.

Figure 7:
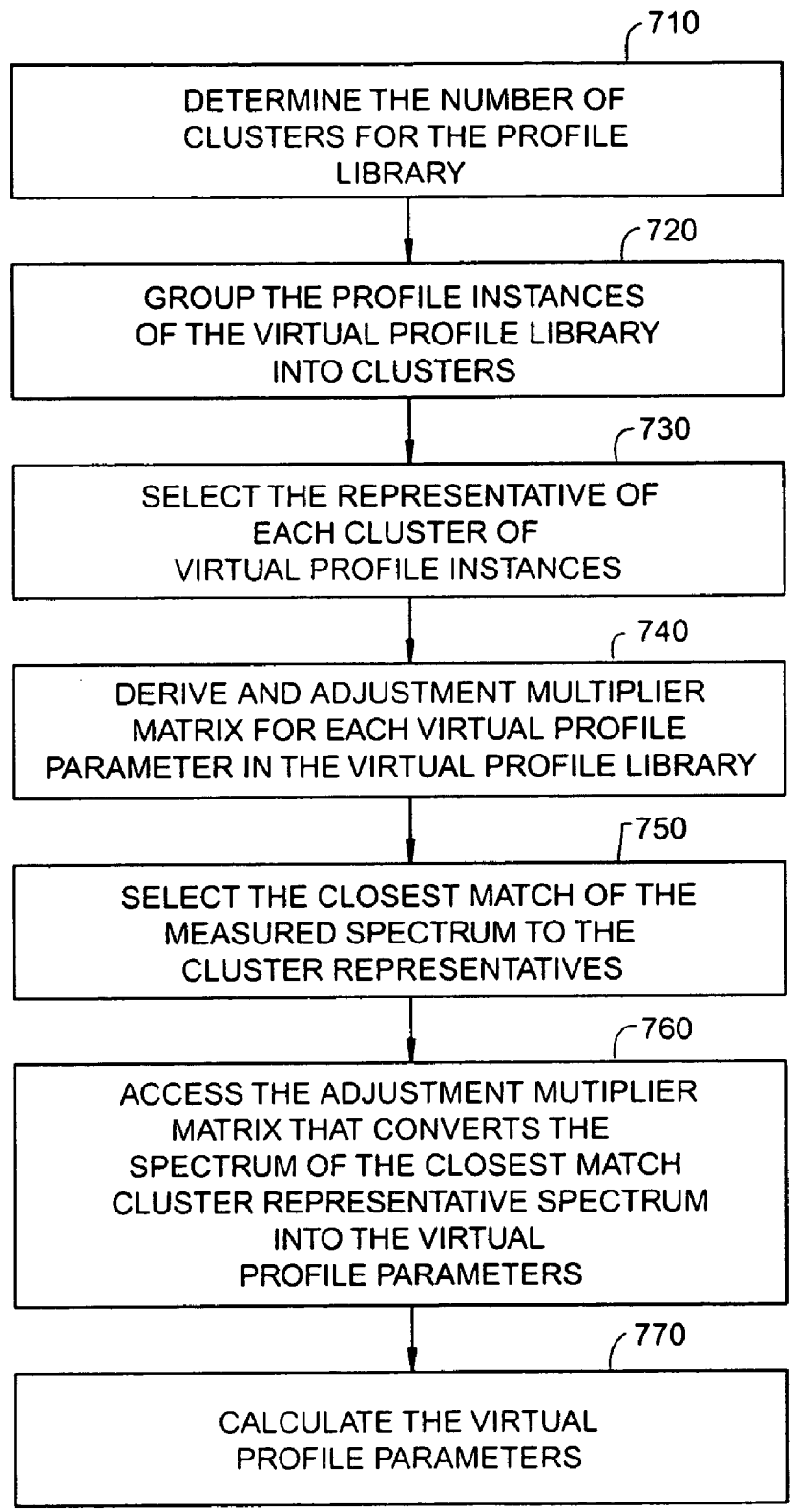
FIG. 7 illustrates a flow chart of a procedure for creating or refining virtual profile library data using clustering of the virtual profile library instances in accordance with embodiments of the invention.

FIG. 7 illustrates a flow chart of a procedure for creating or refining virtual profile library data using clustering of the virtual profile library instances in accordance with embodiments of the invention. As before, the virtual profile refinement process can be performed after creating an un-refined virtual profile library with known and/or unknown inaccuracies. In 710, the number of clusters for the virtual profile library is determined. In 720, a virtual profile instances of the virtual profile library can be grouped into a number of clusters using a clustering algorithm. In 730, a representative of each virtual profile cluster can be selected. The process of clustering-profile library instances and selecting a representative of each profile cluster is described in co-pending U.S. patent application Ser. No. 09/737,705, entitled GRATING PROFILE CLASSIFICATION, by Doddi, et al., filed on Dec. 14, 2000, and is incorporated in its entirety herein by reference.

Still referring to FIG. 7, in 740, an adjustment multiplier matrix for each virtual profile parameter in the virtual profile library can be derived. In some applications, the adjustment multiplier matrix is saved along with the selected cluster representatives. An exemplary embodiment is to solve for X in the following matrix equation:

$$AX=B.$$

A is a measured spectrum matrix of size n'×n, and each row of the matrix corresponds to one spectrum of the measured spectra. B is a virtual profile parameter matrix of size n'×k and each row of the matrix corresponds to one virtual profile parameter. k is the number of virtual profile parameters. n is the number of points measured by the optical metrology device. n' is a number less than or equal to n. X is the adjustment multiplier matrix of size n×k and each row of the matrix corresponds to one virtual profile parameter.

In 750, the measured spectrum is compared to the spectra of the cluster representatives and the closest match is selected. In 760, the adjustment multiplier matrix associated with the closest matching cluster representative can be accessed. In 770, virtual profile parameters can be calculated using the adjustment multiplier matrix and the measured spectrum matrix.

Figure 8:
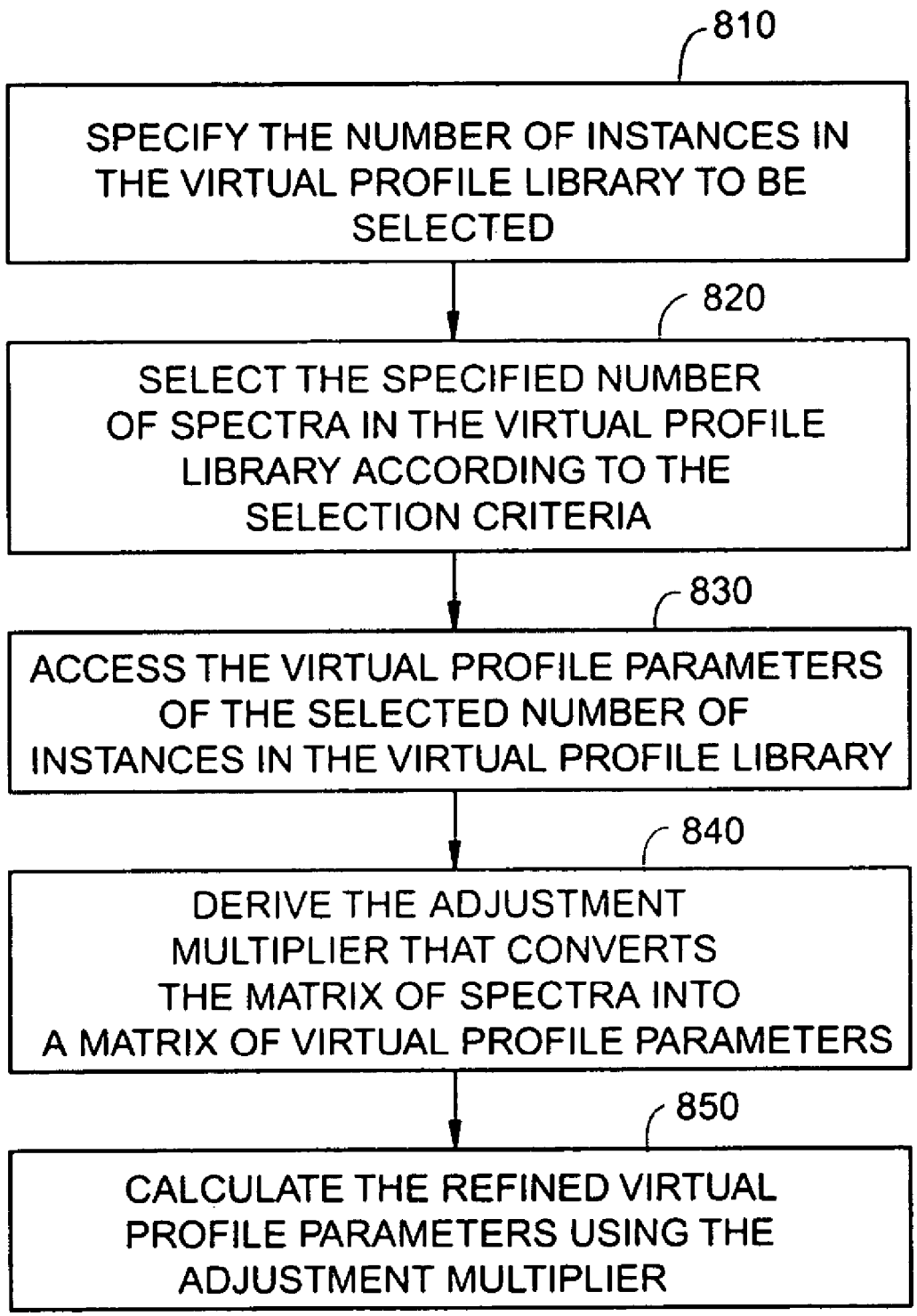
FIG. 8 illustrates a flow chart of a procedure for creating or refining virtual profile library data using adjustment multiplier and cost function optimization in accordance with embodiments of the invention.

FIG. 8 illustrates a flow chart of a procedure for creating or refining virtual profile library data using adjustment multiplier and cost function optimization in accordance with embodiments of the invention. As before, the virtual profile refinement procedure can be performed after creating an un-refined virtual profile library with known and/or unknown inaccuracies. In addition, a virtual profile refinement procedure can be performed after creating a refined virtual profile library to improve the accuracy of the data in the library. In 810, a number can be specified that corresponds to the number of instances in the virtual profile library that will be selected, according to selection criteria, for the virtual profile refinement calculation. The specified number may be varied from run to run. In 820, the specified number of virtual profile library instances can be selected using the selection criteria. For example, the selection of specified number of virtual profile library instances may be based on proximity to a measured spectrum. Alternatively, selection may be based on proximity to the best match spectrum. In 830, the virtual profile parameters of the specified number of virtual profile library spectra instances selected can be accessed. In 840, an adjustment multiplier that converts the matrix of spectra into the matrix of virtual profile parameters can be derived. In 850, virtual profile parameters can be calculated by multiplying the measured diffracted spectrum and the corresponding adjustment multiplier.

Figure 9:
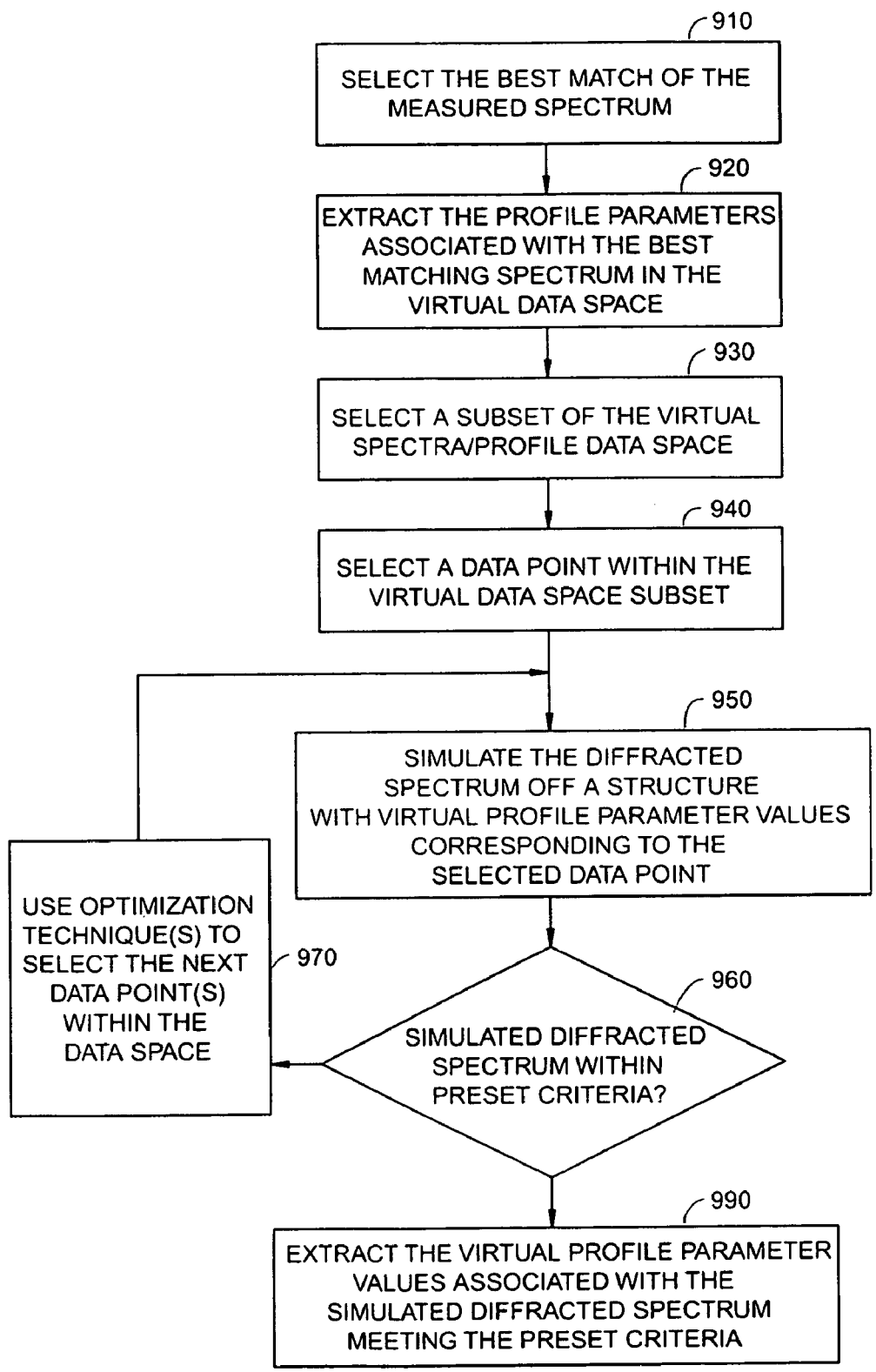
FIG. 9 illustrates a flow chart of a procedure for creating or refining virtual profile library data using a regression-based methodology in accordance with embodiments of the invention.

FIG. 9 illustrates a flow chart of a procedure for creating or refining virtual profile library data using a regression-based methodology in accordance with embodiments of the invention. As before, a virtual profile refinement process can be performed after creating an un-refined virtual profile library with known and/or unknown inaccuracies. In addition, a virtual profile refinement procedure can be performed after creating a refined virtual profile library to improve the accuracy of the data in the library. In 910, a measured diffracted spectrum off a reference/test structure can be compared to the spectra in a virtual profile data space that includes diffracted spectra and associated virtual profile parameters, and a best match spectrum in the virtual profile data space can be selected. In 920, the virtual profile parameters associated with the best match spectrum in the virtual profile data space can be extracted. IN 930, a subset of the virtual profile data space that contains the measured diffracted spectrum and the best match spectrum can be selected. The virtual profile data space subset may be configured to resemble a shape such as a polyhedron, cube, or other three-dimensional shape. In 940, a data point within the virtual profile data space subset can be selected, the selected data point representing a set of associated virtual profile parameters. In 950, a simulated diffracted spectrum off a structure with the virtual profile parameters corresponding to the selected data point is calculated. An exemplary simulation of diffracted spectrum off a structure is described in U.S. patent application Ser. No. 09/764,780, now abandoned, entitled CACHING OF INTRA-LAYER CALCULATIONS FOR RAPID RIGOROUS COUPLED-WAVE ANALYSES, by Niu, et al., filed on Jan. 25, 2001, and is incorporated in its entirety herein by reference.

Still referring to FIG. 9, in 960, the simulated diffracted spectrum off the virtual profile is compared to the measured spectrum and the results are evaluated against virtual profile creation criteria. For example, the virtual profile creation criteria may be a specified error metric value or goodness of fit (GOF), or any measure of closeness of the simulated diffracted spectrum compared to the measured diffracted spectrum. One exemplary matching test that is well known in the art is the Minimum Least Squares Error algorithm. It is understood that other error metric algorithms may also be used. In 970, if the calculated error metric does not meet the preset criteria, then an optimization technique or techniques are used to select additional data points within the virtual data space, and the calculation of the simulated diffracted spectrum is iterated. Exemplary optimization techniques include global optimization techniques such as simulated annealing and local optimization techniques such as the steepest descent algorithm. Use of optimization techniques to generate additional data points corresponding to structure profile parameters is described in U.S. patent application Ser. No. 09/923,578, now U.S. Pat. No. 6,785,638 entitled METHOD AND SYSTEM OF DYNAMIC LEARNING THROUGH A REGRESSION-BASED LIBRARY GENERATION PROCESS, by Niu, et al., filed on Aug. 6, 2001, and is incorporated in its entirety herein by reference.

Still referring to FIG. 9, in 990, the virtual profile parameters associated with the simulated diffracted spectrum meeting the preset criteria can be accessed, these values being the refined virtual profile parameters.

Figure 10A:
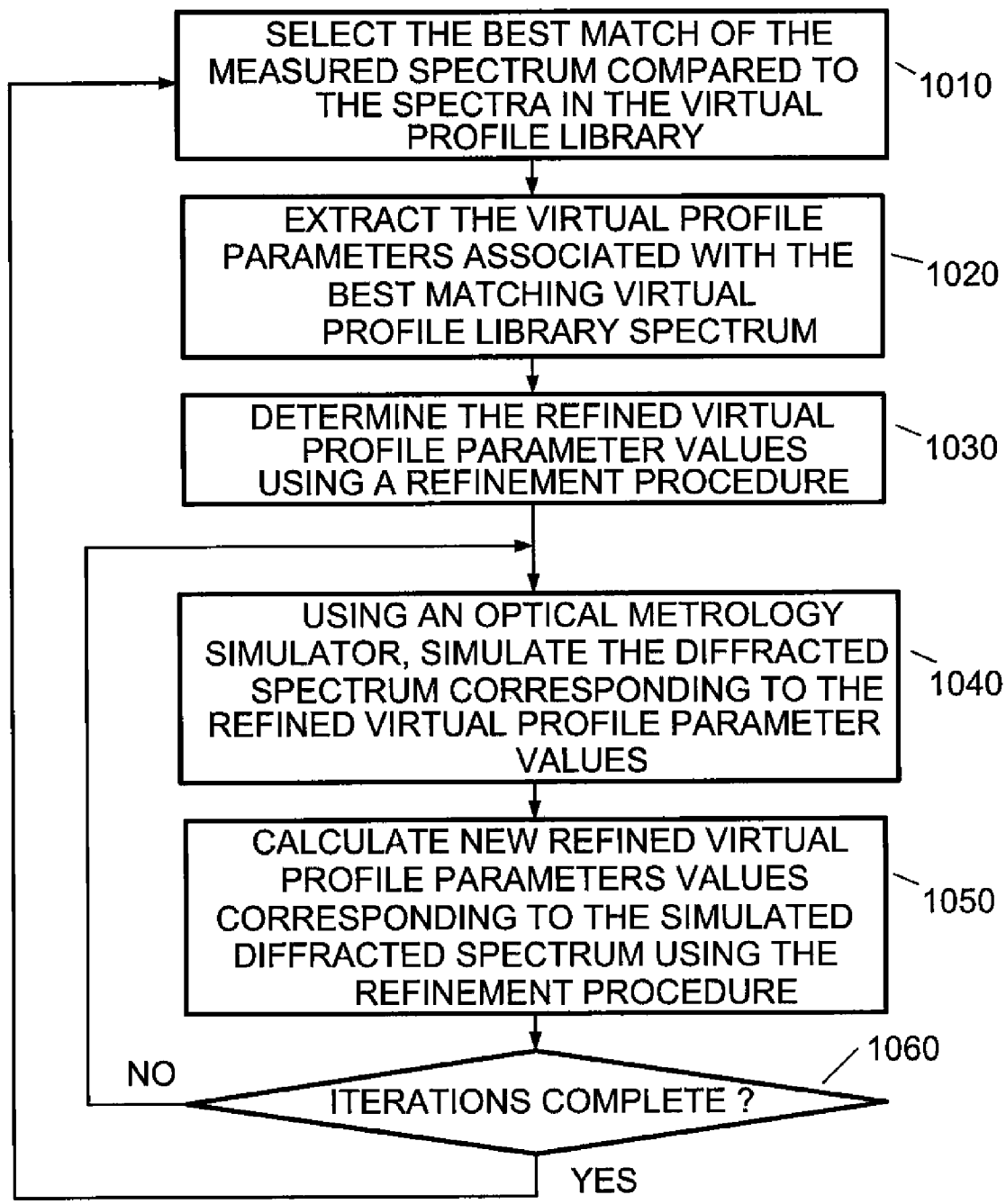
FIG. 10A illustrates a flow chart of a procedure for creating or refining virtual profile library data using a localized fine-resolution refinement library method in accordance with embodiments of the invention.

FIG. 10A illustrates a flow chart of a procedure for creating or refining virtual profile library data using a localized fine-resolution refinement library method in accordance with embodiments of the invention. Some refinement and/or accuracy improvement procedures methods assume that the diffracted spectrum responds to changes in the profile parameters in a linear manner within the library data points. The present method corrects for the non-linearity effect. As such, the present method may be used with any virtual profile library. In 1010, the measured diffracted spectrum from a reference/test structure can be compared to the diffracted spectra in the virtual profile library, and a best match can be selected. In 1020, the virtual profile parameters associated with the best matching spectrum in the virtual profile library can be extracted. Virtual profile parameters can be calculated using the procedure described below.

To illustrate the method, assume a 2-dimensional virtual profile parameter space with $vp_1$ and $vp_2$ as the two dimensions as illustrated in FIG. 10B. In 1030, the first virtual profile parameter data point can be determined from the equation:

$$vp^{R1}=vp^0+(J^TJ)^{-1}J^T(S^M-S^0).$$

$S^M$ is the measured spectrum, $vp^{R1}$ is the first calculated virtual profile parameters for the measured spectrum $S^M$. $vp^0$ is the profile data point corresponding to the best match library spectrum $S^0$. J is the sensitivity matrix derived in a similar manner as discussed in FIG. 6A. If the diffracted spectrum response to changes in the virtual profile parameters were linear within the virtual profile library data points, then the refined virtual profile spectrum $S^R$ associated with $vp^{R1}$ would be calculated with the following equation:

$$S^R=S^0+J(vp^{R1}-vp^0).$$

However, due to the non-linearity effect, $S^R$ is not the "true number" or the accurate diffracted spectrum for virtual profile parameter data point $vp^{R1}$. In 1040, in order to compensate for the non-linearity, an accurate calculation of the diffracted optical metrology spectrum for the set of profile parameters associated with $vp^{R1}$ is performed using an optical metrology simulator, generating an accurate spectrum $S^{RA}$. The process of calculating a spectrum using optical metrology simulation techniques is described in U.S. patent application Ser. No. 09/764,780, now abandoned, entitled CACHING OF INTRA-LAYER CALCULATIONS FOR RAPID RIGOROUS COUPLED-WAVE ANALYSES, by Niu, et al., filed on Jan. 25, 2001 and is incorporated herein by reference. In 1050, the second calculated or revised virtual profile parameter data point, $vp^{R2}$, is calculated, using the equation:

$$vp^{R2} = vp^{R1} + (J^T J)^{-1} J^T (S^M - S^{RA}).$$

$(S^M - S^{RA})$ is less than $(S^M - S^0)$, thus the non-linearity effect is less and the virtual profile parameter data point $vp^{R2}$ is closer to the virtual profile parameters $vp^M$ of the measured spectrum $S^M$. Referring to FIG. 10B, the data point $vp^{R2}$ corresponding to $S^{RA}$ is closer to $vp^M$ corresponding to the measured spectrum $S^M$.

Referring again to FIG. 10A, depending on user selected options, the simulation step 1040 and the calculation of revised virtual profile parameter data points 1050 may be iterated a number of times in 1060. As number of iterations increases, the non-linearity effect is reduced, resulting in more accurate virtual profile parameters.

Figure 11:
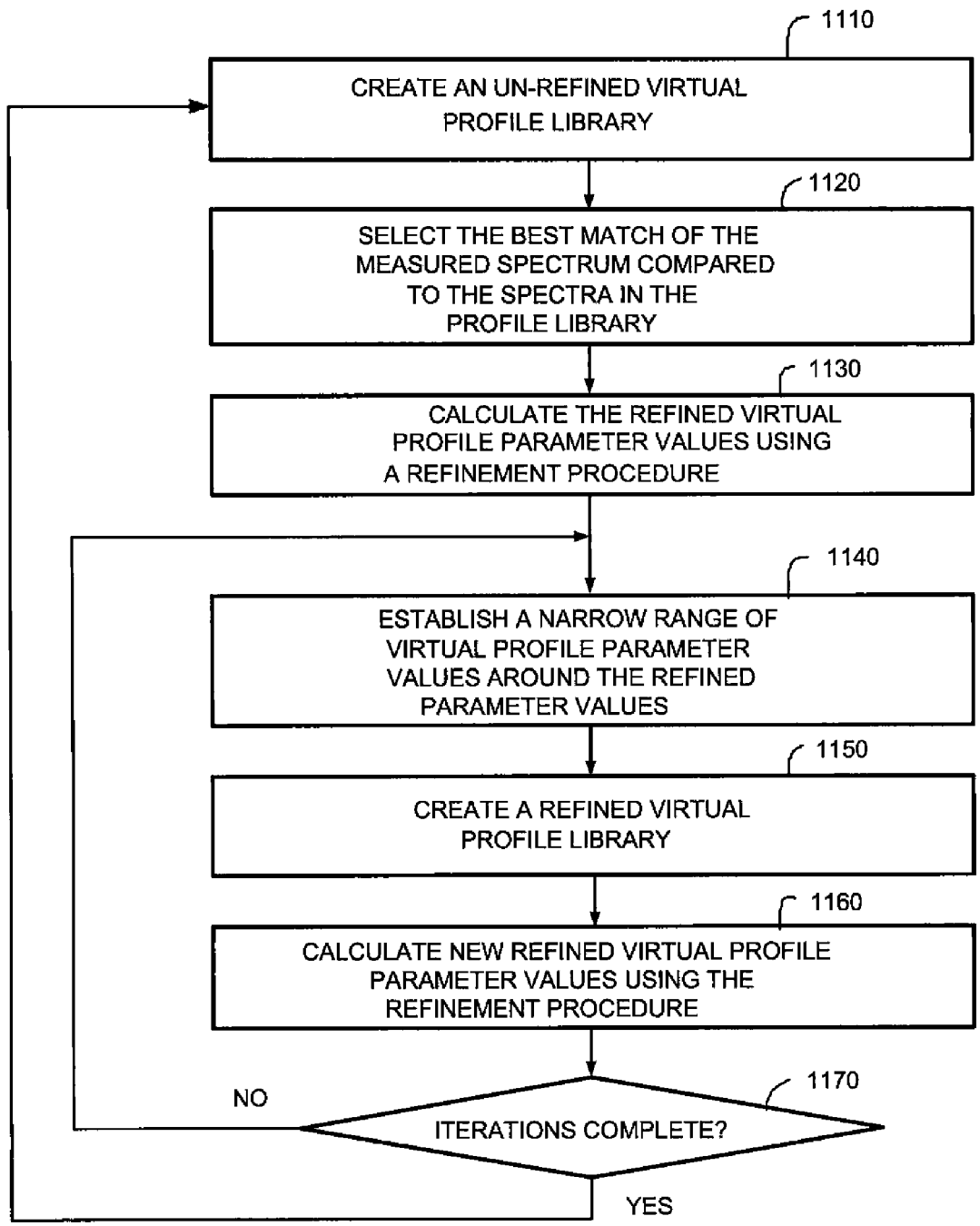
FIG. 11 illustrates a flow chart of a procedure for creating and/or refining an unrefined virtual profile library in accordance with embodiments of the invention.

FIG. 11 illustrates a flow chart of a procedure for creating and/or refining an unrefined virtual profile library in accordance with embodiments of the invention. In 1110, an un-refined virtual profile library can be created. For example, an un-refined virtual profile library may be created with inaccurate profile data, inaccurate signal data, a large step size resolution, and with a wide range of virtual profile parameters. In 1120, using a measured spectrum from a reference/test structure, the measured spectrum can be compared to the spectra in the virtual profile library, and a best match can be selected. In 1130, new virtual profile parameters can be determined by using an accuracy improvement and/or refinement procedure. For example, any of the previously discussed procedures or other commercially available procedures may be used. In 1140, a refined (narrower) range of virtual profile parameters can be established around the refined virtual profile parameters. For example, a smaller accuracy window (FIG. 3) may be established around a data point in the virtual profile data space. The choice of the new, narrower (refined) range of the virtual profile parameters can be a based on the IC structures being manufactured. For example, for a trapezoidal profile with three profile parameters, namely, top CD, bottom CD, and height, the narrower top CD range may be one increment in the positive direction from the virtual profile parameter value and one increment in the negative direction. The narrower range for the bottom CD may likewise be set to one increment in the positive direction and one increment in the negative direction, and so on. In 1150, a refined virtual profile library for the new range of profile parameters can be established around the virtual profile values with a finer step-size resolution can be created. For example, the coarse library resolution may be 20 nanometers (nm). The first iteration of creating a finer stepsize resolution may result in a resolution of 15 nm, the second iteration may result in a resolution of 8 nm, and so on. In 1160, the revised virtual profile parameters can be determined by using the same or a different procedure, and the new successively finer stepsize-resolution libraries can be created. In 1170, depending on user selected options, the steps of establishing the virtual profile parameter range, creating the new virtual profile library, and calculating the revised virtual profile parameters may be iterated a number of times. As the number of iterations increases, the virtual profile library resolution increases in a progressively smaller space, resulting in more accurate virtual profile parameters.

Figure 12:
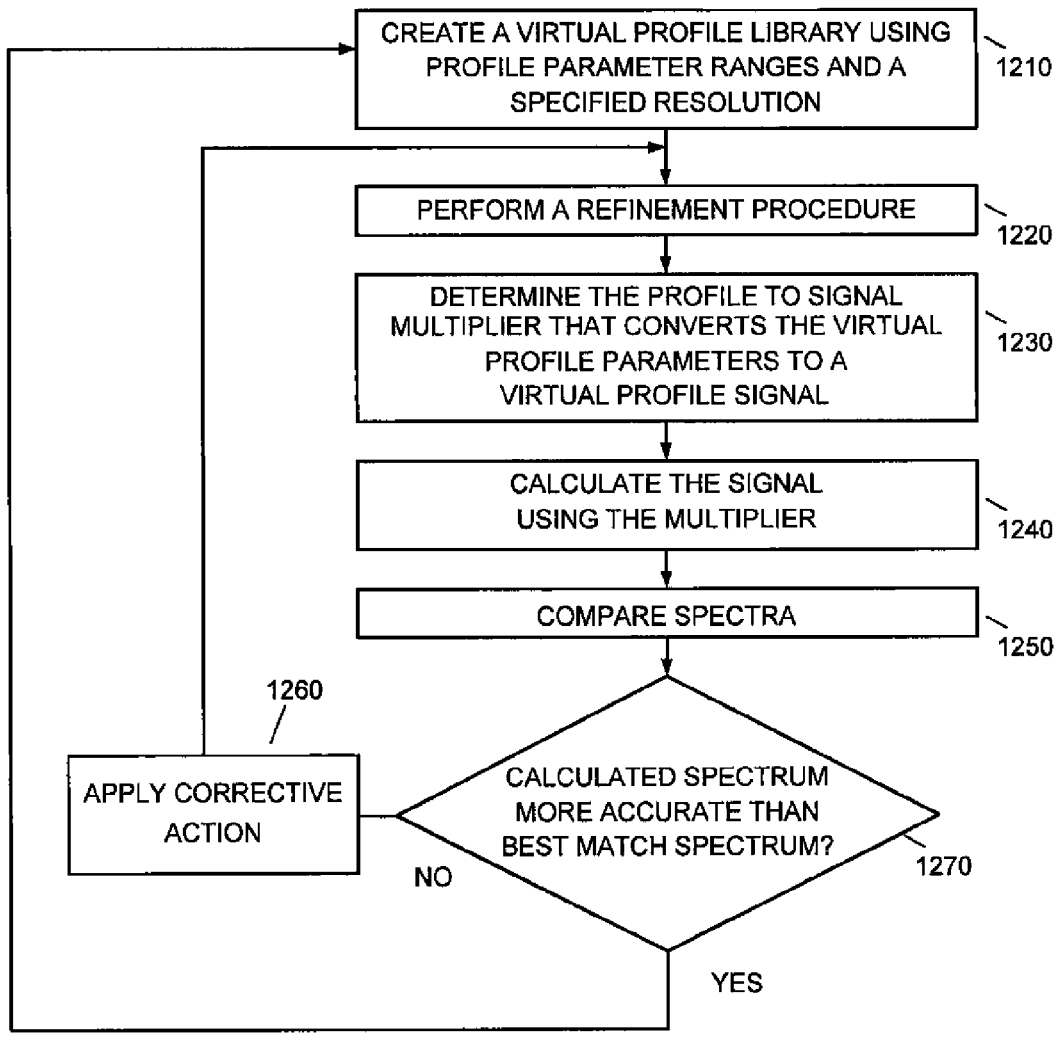
FIG. 12 is a flow chart of a procedure for verifying the accuracy of the refined virtual profile parameter versus the best match virtual profile parameter in accordance with embodiments of the invention.

FIG. 12 is a flow chart of a procedure for verifying the accuracy of the refined virtual profile parameter versus the best match virtual profile parameter in accordance with embodiments of the invention. Refinement accuracy checking can be done during testing the of the virtual profile refinement procedures and/or during the creation of the virtual profile libraries. In 1210, when a virtual profile library is created, specified ranges of the virtual profile parameters and specified resolutions and/or accuracies can be established. Creation of a profile library is described in co-pending U.S. patent application Ser. No. 09/727,530, entitled SYSTEM AND METHOD FOR REAL-TIME LIBRARY GENERATION OF GRATING PROFILES, by Jakatdar, et al., filed on Nov. 28, 2000, and is incorporated in its entirety herein by reference.

In 1220, a refinement calculation can be performed using one or more of the refinement procedures and/or methods discussed above. In 1230, a virtual profile to spectrum multiplier Y that converts the virtual profile parameters to a refined (more accurate) virtual profile spectra can be determined. The adjustment multiplier from profile to spectrum can be calculated using the equation described in FIG. 7 and designating the adjustment multiplier matrix as Y. In 1240, the refined virtual profile signal (diffracted spectrum) can be calculated using the profile to signal/spectrum multiplier Y and the virtual profile parameters as expressed the following matrix equation:

$$EY = G.$$

G is the refined virtual profile spectra matrix of size 1×n, and each row of the matrix corresponds to one measurement of the measured spectrum. E is a virtual profile parameter matrix of size 1×k and each row of the matrix corresponds to one virtual profile parameter. k is the number of virtual profile parameters. n is the number of points measured by the optical metrology device. Y is the adjustment multiplier matrix of size k×n and each row of the matrix corresponds to one virtual profile parameter.

In 1250, the accuracy of the refined virtual profile spectrum relative to the measured spectrum is compared to the accuracy of the best match spectrum relative to the measured spectrum. One method involves comparing the cost function of the refined virtual profile spectrum relative to the best matching spectrum versus the cost function of the measured spectrum relative to the best matching spectrum. The cost function comparison is illustrated by the equations below.

Assume $V_1$ and $V_2$ are two vectors of size n, then the cost function of $V_1$ relative to $V_2$ can be expressed as:

$$\text{Cost}(V_1, V_2) = \sqrt{\sum_{i=1}^{n} (V_{1i} - V_{2i})^2}.$$

A similar cost function can be calculated for $V_1$ relative to $V_3$, a third vector of size n.

It is understood that other cost optimization techniques may be used; furthermore, other techniques may also be used to compare relative accuracy of matrices and vectors. Still referring to FIG. 12, if the refined virtual profile spectrum is more accurate than the best match spectrum 1270, or a threshold goodness of fit is met, then the refinement setup is adequate. For example, if $V_1$ is the measured spectrum, $V_2$ is the refined virtual profile spectrum, and $V_3$ is the best match spectrum, then if $Cost(V_1, V_2) < Cost(V_1, V_3)$, the refinement setup is considered adequate. Otherwise, parameters of the virtual profile library compilation are adjusted or a corrective action is applied 1260 and the process is iterated starting at step 1210. Several examples of corrective actions include recreating the virtual profile library at a higher resolution or lowering the threshold deviation during the calculations of refined virtual profile resolution. Alternatively, other refinement procedures described above or known in the trade may be used.

Figure 13A:
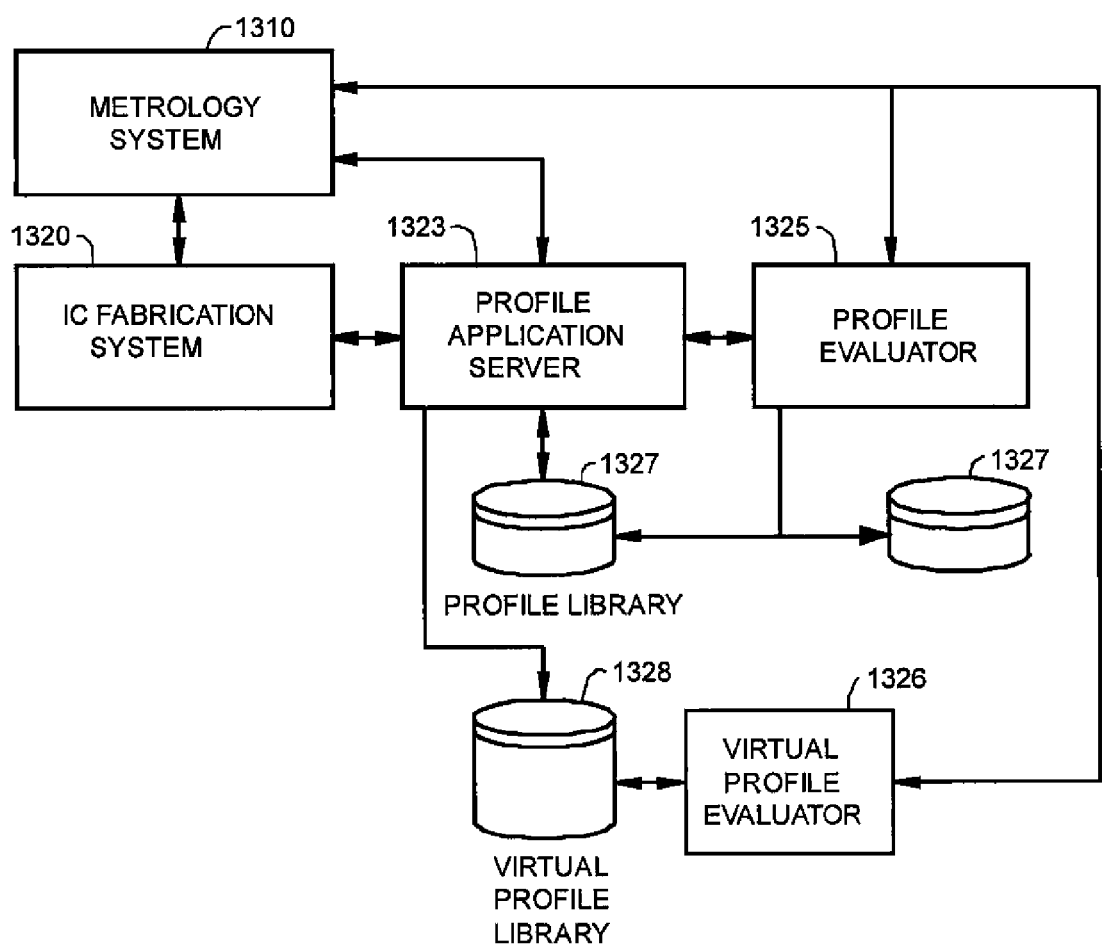

FIG. 13A is an architectural diagram illustrating a system for creating, refining, and/or using a virtual profile library in accordance with embodiments of the invention. In the illustrate embodiment, profile evaluators 1325 and virtual profile evaluators 1326 are shown but this is not required for the invention. Alternatively, other system configurations may be used. An IC fabrication system 1320 such as lithography, etch, deposition, or stripping unit is coupled to a metrology system 1310. The metrology system 1310 may be an optical, electric, electron, or mechanical metrology system. Examples of optical metrology systems include scatterometric devices such as spectroscopic ellipsometers and reflectometers. Examples of electron metrology systems include CD-scanning electron microscope (CD-SEM), transmission electron microscope (TEM), and focused ion beam (FIB) devices. An example of a mechanical metrology system includes an atomic force microscope (AFM) whereas an example of an electric metrology system includes a capacitance-measuring unit. The metrology system 1310 can be coupled to a profile application server 1323, to a profile evaluator 1325, and/or virtual profile evaluator 1326. The metrology system 1310 measures an IC structure and generates a measured signal and transmits the measured signal to the profile application server 1323.

The profile application server 1323 can access the profile library 1327 in order to find the best match signal in the profile library 1327. In addition, the profile application server 1323 can access the virtual profile library 1328 in order to find the best match signal in the virtual profile library 1328. If predetermined criteria of acceptability are not met, for example, an error metric is not met, then the profile evaluator 1325 and/or the virtual profile evaluator 1326 can be invoked. Alternatively, the profile evaluator 1325 and/or the virtual profile evaluator 1326 may be invoked based on some other criteria or invoked automatically by the profile application server 1323. In some applications, the profile evaluator 1325 and/or the virtual profile evaluator 1326 may be invoked automatically and/or directly by the metrology system 1310. The profile evaluator 1325 either accesses the profile library 1327 directly or through the profile application server 1323. The profile evaluator 1325 transmits the parameters back to the profile application server 1323 and the profile application server 1323 in turn makes the information available to the IC fabrication system 1320. Alternatively, the profile evaluator 1325 transmits the parameters back to the metrology system 1310. The profile library 1327 may be a physical library in a storage device or a data store in a computer memory or a data store in a storage device. Refined parameters are profile parameters calculated using refinement methods and procedures, several of which are described below. A profile evaluator 1325 can comprise hardware, software, or firmware capable of executing the profile analysis methods and procedures.

The virtual profile evaluator 1326 can either access the virtual profile library 1328 directly or through the profile application server 1323. The virtual profile evaluator 1326 can transmit the virtual profile parameters back to the virtual profile application server 1326 and the virtual profile application server 1326 in turn makes the information available to the IC fabrication system 1320. Alternatively, the virtual profile evaluator 1326 transmits the virtual profile parameters back to the metrology system 1310. The virtual profile library 1328 may be a physical library in a storage device or a data store in a computer memory or a data store in a storage device. Virtual profile parameters are profile parameters calculated using virtual profile and/or virtual library methods and procedures, several of which are described below. A virtual profile evaluator 1326 can comprise hardware, software, and/or firmware capable of executing the virtual profile methods and procedures.

Figure 13B:
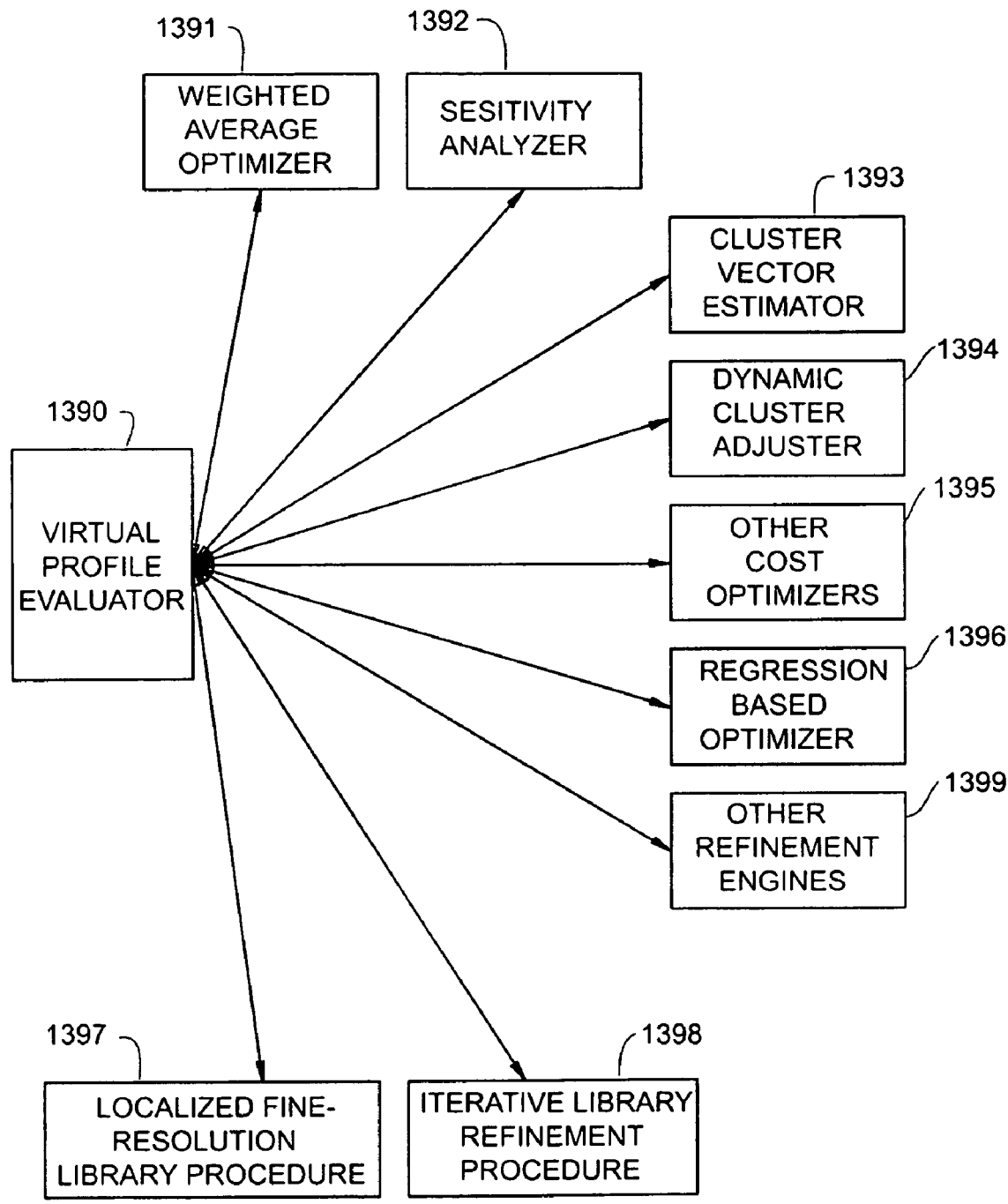
FIG. 13B is an architectural diagram illustrating a virtual profile evaluator invoking various cost optimizers and refinement engines in accordance with embodiments of the invention.

FIG. 13B is an architectural diagram illustrating a virtual profile evaluator invoking various cost optimizers and refinement engines in accordance with embodiments of the invention. The virtual profile evaluator 1390 may activate one or more types of virtual profile library engines to get the desired virtual profile results based on specified acceptance criteria. A virtual profile library engine may be a software, firmware, or hardware capable of performing the operational steps of creation and/or verification given measured signals and a data space comprising signals and associated virtual profile parameters. A weighted average optimizer 1391, sensitivity analyzer 1392, cluster vector estimator 1393, dynamic cluster adjuster 1394, or other cost function optimizers 1395 may be used to generate the virtual profile parameters using measured signals and a set of signals and associated profile parameters. A regression-based optimizer 1396 may be used wherein data points within a data space of signals and virtual profile parameters are successively evaluated for goodness of fit compared to the measured spectrum.

Alternatively, the virtual profile evaluator 1390 may use a localized fine-resolution library procedure 1397 or an iterative library refinement procedure 1398. Other refinement engines 1399 may use a refinement technique such as bilinear refinement, Lagrange refinement, Cubic Spline refinement, Aitken refinement, weighted average refinement, multi-quadratic refinement, bi-cubic refinement, Turran refinement, wavelet refinement, Bessel's refinement, Everett refinement, finite-difference refinement, Gauss refinement, Hermite refinement, Newton's divided difference refinement, osculating refinement, Thiele's refinement algorithm or other refinement algorithms.

The profile evaluator generally require a specified extent of non-linearity between virtual profile parameter and spectrum data points in order to generate virtual profile parameters of structures that provide a specified level of accuracy. To achieve consistent results, a linearity test or procedure is required. The extent of non-linearity between profile library data points can be ensured by either empirical methods or by the use of mathematical algorithms.

Business rules can be used to specify the action taken for normal processing and the actions taken on exceptional conditions. Business rules can be defined at a control strategy level, a control plan level or a control model level. Business rules can be assigned to execute whenever a particular context is encountered. When a matching context is encountered at a higher level as well as a lower level, the business rules associated with the higher level can be executed. GUI screens can be used for defining and maintaining the business rules. Business rule definition and assignment can be allowed for users with greater than normal security level. The business rules can be maintained in the database. Documentation and help screens can be provided on how to define, assign, and maintain the business rules. Business rules can be used to determine which processes are monitored and which data is used.

Foregoing described embodiments of the invention are provided as illustrations and descriptions. They are not intended to limit the invention to precise form described. For example, as discussed above, the concepts and principles of the present invention will apply to other refinement algorithms, procedures, and/or methods. Furthermore, as discussed in FIG. 12, the concepts and principles of the present invention apply to many types of metrology devices that measure signals off an IC structure and correlate the signals to profiles of the structures. In addition to optical metrology simulators, other metrology simulators perform similar functions as the optical metrology simulator in simulating the signals for a set of profile parameters.

In particular, it is contemplated that functional implementation of the present invention described herein may be implemented equivalently in hardware, software, firmware, and/or other available functional components or building blocks. Other variations and embodiments are possible in light of above teachings, and it is thus intended that the scope of invention not be limited by this Detailed Description, but rather by Claims following.

What is claimed is:

1. A method of creating a virtual profile library, the method comprising:
   obtaining a reference signal, wherein the reference signal was generated by measuring a signal off a reference structure on a semiconductor wafer with a metrology device;
   comparing the reference signal to a plurality of signals in a first library, and stopping the comparing when a first goodness of fit value is met;
   comparing the reference signal to a plurality of signals in a second library, and stopping the comparing when a second goodness of fit value is met;
   creating a virtual profile data space when the first and second goodness of fit values are not met, wherein the virtual profile data space is created using differences between a profile data space associated with the first library and a profile data space associated with the second library;
   creating a first virtual profile signal in the virtual profile data space;
   creating a virtual profile shape and/or virtual profile parameters based on the first virtual profile signal; and
   calculating a difference between the reference signal and the first virtual profile signal;
   comparing the difference to a virtual profile library creation criteria; and either
   storing in the virtual profile library the first virtual profile signal and the virtual profile data, which includes the virtual profile shape and/or virtual profile parameters, associated with the first virtual profile signal when the virtual profile library creation criteria is met, or applying a corrective action when the virtual profile library creation criteria is not met.

2. The method of claim 1, wherein the first virtual profile signal is created using a difference between a signal in the first library and a signal in the second library.

3. The method of claim 1, wherein applying a corrective action comprises:
   creating a new virtual profile signal of the virtual profile data space, wherein a new virtual profile shape and/or new virtual profile parameters are created based on the new virtual profile signal, wherein an optimization technique is performed to select the new virtual profile signal;
   calculating a difference between the reference signal and the new virtual profile signal;
   comparing the difference to a virtual profile library creation criteria; and either
   storing the newly created virtual profile signal and new virtual profile data, which includes the new virtual profile shape and/or new virtual profile parameters, associated with the newly created virtual profile signal when the virtual profile library creation criteria is met, or stopping the creating, the calculating, and the comparing, when the virtual profile library creation criteria is not met.

4. The method of claim 3, wherein the new virtual profile signal is created using a new difference between a signal in the first library and a signal in the second library.

5. The method of claim 3, wherein the optimization technique involves applying a global optimization technique and/or a local optimization technique.

6. The method of claim 1, wherein the virtual profile library creation criteria includes a goodness of fit value.

7. The method of claim 1, wherein the first virtual profile signal is created in real time using differences between the signals in the first library and the signals in the second library.

8. The method of claim 1, wherein the first virtual profile signal is created in real time using differences between profile shapes in the first library and profile shapes in the second library.

9. The method of claim 1, wherein the first virtual profile signal is created using a plurality of virtual profile signals in the virtual profile library.

10. The method of claim 1, wherein the difference between the reference signal and the first virtual profile signal is determined at a plurality of wavelengths.

11. The method of claim 10, wherein the plurality of wavelengths comprise wavelengths from approximately 100 nm to approximately 1000 nm.

12. The method of claim 1, further comprising:
    creating a first cluster space within the virtual profile data space, wherein the first cluster space is created using differences between a second cluster space associated with the first library and a third cluster space associated with the second library;
    creating a second virtual profile signal within the first cluster space, the first cluster space containing the reference signal and data points proximate to the data point associated with the second virtual profile signal;
    calculating a difference between the reference signal and the second virtual profile signal;
    comparing the difference to a virtual profile cluster creation criteria; and either
    storing the data point associated with the second virtual profile signal in the virtual library as a member of the first cluster space when the virtual profile cluster creation criteria is met, or applying a corrective action when the virtual profile cluster creation criteria is not met.

13. The method of claim 12, wherein applying a corrective action comprises:
    creating a new virtual profile signal within the first cluster space, the first cluster space containing the reference signal and data points proximate to the data point associated with the newly created virtual profile signal;
    calculating a difference between the reference signal and the newly created virtual profile signal;

comparing the difference to a virtual profile cluster creation criteria; and either storing the data point associated with the newly created virtual profile signal in the virtual library as a member of the first cluster space when the virtual profile cluster creation criteria is met, or stopping the creating, the calculating, and the comparing, when the virtual profile cluster creation criteria is not met.

14. The method of claim 1, further comprising:

creating a first cluster space within the virtual profile data space, wherein the first cluster space is created using differences between a second cluster associated with the first library and a third cluster associated with the second library;

creating a virtual profile within the first cluster space, the first cluster space containing the reference signal and data points proximate to the data point associated with the created virtual profile;

simulating a signal off a structure with virtual profile parameters corresponding to the created virtual profile;

calculating a difference between the reference signal and the simulated signal;

comparing the difference to a virtual profile cluster creation criteria; and either storing the data point associated with the created virtual profile in the virtual library as a member of the first cluster space when the virtual profile cluster creation criteria is met, or applying a corrective action when the virtual profile cluster creation criteria is not met.

15. The method of claim 14, wherein applying a corrective action comprises:

creating a new virtual profile within the first cluster space, the first cluster space containing the reference signal and data points proximate to the data point associated with the newly created virtual profile;

simulating a new signal off a structure with virtual profile parameters corresponding to the newly created virtual profile;

calculating a difference between the reference signal and the new simulated signal;

comparing the difference to a virtual profile cluster creation criteria; and either storing the data point associated with the newly created virtual profile in the virtual library as a member of the first cluster space when the virtual profile cluster creation criteria is met, or stopping the creating, the calculating, and the comparing, when the virtual profile cluster creation criteria is not met.

16. The method of claim 1, further comprising:

determining a reference profile associated with the reference signal;

creating a virtual profile in the virtual profile data space, wherein a virtual profile signal and/or virtual profile parameters are determined based on the virtual profile; and calculating a difference between the reference profile and the created virtual profile;

comparing the difference to a virtual profile library creation criteria; and either storing the created virtual profile and virtual profile data, which includes the virtual profile signal and/or virtual profile parameters, associated with the created virtual profile when the virtual profile library creation criteria is met, or applying a corrective action when the virtual profile library creation criteria is not met.

17. The method of claim 16, wherein applying a corrective action comprises:

creating a new virtual profile in the virtual profile data space, wherein a new virtual profile signal and/or new virtual profile parameters are created based on the new virtual profile, wherein an optimization technique is performed to select the new virtual profile signal;

calculating a difference between the reference profile and the new virtual profile;

comparing the difference to a virtual profile library creation criteria; and either storing the newly created virtual profile and new virtual profile data, which includes the new virtual profile signal and/or new virtual profile parameters, associated with the newly created virtual profile when the virtual profile library creation criteria is met, or stopping the creating, the calculating, and the comparing, when the virtual profile library creation criteria is not met.

18. The method of claim 1, wherein creating the first virtual profile signal further comprises:

computing a virtual profile sensitivity matrix, the virtual profile sensitivity matrix being a measure of the change of a virtual profile signal induced by a change of a virtual profile parameter, wherein the virtual profile sensitivity matrix is determined using a sensitivity matrix associated with the first library, or a sensitivity matrix associated with the second library, or a combination thereof;

determining an adjustment value of the virtual profile parameters using the computed sensitivity matrix, and creating the virtual profile parameters by adding the adjustment value of the virtual profile parameters to corresponding profile parameters of a best estimate data point in the first library, or a best estimate data point in the second library, or a best estimate data point outside the libraries.

19. The method of claim 1, wherein creating the first virtual profile signal further comprises:

computing an adjustment matrix, the adjustment matrix including an adjustment value for at least one virtual profile parameter, wherein each adjustment value is determined using a profile parameter associated with a profile of the first library, or a profile parameter associated with a profile of the second library, or a combination thereof;

creating a virtual profile by using the adjustment matrix and the profile parameters associated with the first library, or the profile parameters associated with the second library, or profile parameters associated with a data point outside the libraries; and creating the first virtual profile signal by simulating a signal off a structure with virtual profile parameters corresponding to the created virtual profile.

20. The method of claim 1, wherein creating the first virtual profile signal further comprises:

computing an adjustment matrix, the adjustment matrix including an adjustment value for at least one virtual profile signal, wherein each adjustment value is determined using a diffraction signal associated with a profile of the first library, or a diffraction signal associated with a profile of the second library, or a combination thereof; and creating the first virtual profile signal by using the adjustment matrix and the diffraction signals associated with the first library, or the diffraction signals associated with the second library, or diffraction signals associated with a data point outside the libraries.

21. The method of claim 1, wherein creating the first virtual profile signal further comprises:

creating a best estimate of the reference signal in the virtual profile data space, wherein the best estimate being created using differences between a profile data space associated with the first library and a profile data space associated with the second library, the virtual profile data space having data points with specified accuracy values, the virtual profile parameters providing a characterization of a profile of an integrated circuit structure, the best estimate being a data point of the virtual profile data space with a signal closest to the reference signal;

creating a polyhedron in the virtual profile data space, the polyhedron containing the best estimate data point and having corners corresponding to selected profile parameter data points proximate to the best estimate data point;

minimizing a total cost function, the total cost function comprising a cost function of the signals corresponding to the selected profile parameter data points relative to the reference signal and a cost function of the best estimate signal relative to the reference signal; and storing the first virtual profile signal when the minimization is successful.

22. The method of claim 21, wherein the created polyhedron has at least one corner associated with each profile parameter.

23. The method of claim 21, wherein minimizing the total cost function comprises:

selecting a set of weighting vectors, each weighting vector having vector elements, each vector element associated with the first virtual profile signal corresponding to a selected data point;

calculating the total cost function for each weighting vector of the set of weighting vectors; and selecting the weighting vector that yields the minimum total cost function.

24. The method of claim 23, further comprising:

creating the first virtual profile signal using the weighting vector associated with the minimum total cost function.

25. The method of claim 1, further comprising:

determining an accuracy value for the first virtual profile signal;

comparing the accuracy value against accuracy limits; and performing a refinement procedure if the accuracy value does not meet the accuracy limits.

26. The method of claim 25, further comprising:

creating refined virtual profile parameters corresponding to the reference signal using the refinement procedure;

verifying that a refined virtual profile creation criteria is met, the refined virtual profile creation criteria comprising a measure of goodness of fit of a refined simulated signal of a refined virtual profile relative to the reference signal; and extracting refined virtual profile parameters associated with the refined simulated signal that meet the refined virtual profile creation criteria.

27. The method of claim 25, wherein the refinement procedure utilizes bilinear refinement, Lagrange refinement, Cubic Spline refinement, Aitken refinement, weighted average refinement, multi-quadratic refinement, bi-cubic refinement, Turran refinement, wavelet refinement, Bessel's refinement, Everett refinement, finite-difference refinement, Gauss refinement, Hermite refinement, Newton's divided difference refinement, osculating refinement, or Thiele's refinement algorithm, or a combination thereof.

28. The method of claim 1, further comprising:

creating an unrefined virtual profile library using unrefined data having unrefined accuracy limits;

creating refined accuracy limits for a refined virtual profile library; and comparing the calculated difference to a refined accuracy limit; and either storing the first virtual profile signal and the virtual profile data associated with the first virtual profile signal in a refined virtual library, when the refined accuracy limit is met, or storing the first virtual profile signal and the virtual profile data associated with the first virtual profile signal in an unrefined virtual library, when the refined accuracy limit is not met.

29. The method of claim 28, further comprising:

creating an unrefined accuracy value for an unrefined virtual profile, an unrefined virtual profile signal, or a set of unrefined virtual profile parameters, or a combination thereof; and creating a refined accuracy value for a refined virtual profile, a refined virtual profile signal, or a set of refined virtual profile parameters, or a combination thereof.

30. The method of claim 1, wherein the reference structure is verified using CD-scanning electron microscope (CD-SEM) data, transmission electron microscope (TEM) data, and/or focused ion beam (FIB) data.

31. A method of expanding a virtual profile library, the method comprising:

obtaining a measured signal, wherein the measured signal was generated by measuring a signal off a structure with a metrology device;

calculating a difference between the measured signal and a refined virtual profile signal in a refined virtual profile library;

comparing the difference to a refined virtual profile library creation criteria; and either storing virtual profile library data associated with the structure as refined virtual profile library data in the virtual profile library when the refined virtual profile library creation criteria is met, or applying a first corrective action when the refined virtual profile library creation criteria is not met, wherein applying a first corrective action comprises:

calculating a second difference between the measured signal and an unrefined virtual profile signal in an unrefined virtual profile library;

comparing the second difference to an unrefined virtual profile library creation criteria; and either storing the virtual profile library data associated with the structure and unrefined virtual profile data associated with the unrefined virtual profile signal when the unrefined virtual profile library creation criteria is met, or applying a second corrective action when the unrefined virtual profile library creation criteria is not met, wherein applying a second corrective action comprises:

creating a new unrefined virtual profile signal in the unrefined virtual profile data space, wherein a new unrefined virtual profile shape and/or new unrefined virtual profile parameters are created based on the new unrefined virtual profile signal; and calculating a third difference between the measured signal and the new created unrefined virtual profile signal;

comparing the third difference to an unrefined virtual profile library creation criteria; and either storing the new created unrefined virtual profile signal and unrefined virtual profile data, which includes the new unrefined virtual profile shape and/or new unrefined virtual profile parameters, associated with the created unrefined virtual profile signal in an unrefined virtual profile library, when the virtual profile library creation criteria is met, or applying a third corrective action when the unrefined virtual profile library creation criteria is not met, and wherein applying a third corrective action comprises:

determining an accuracy value for the new created unrefined virtual profile signal;

comparing the accuracy value against accuracy limits; and performing a refinement procedure when the accuracy value does not meet the accuracy limits.

32. The method of claim 31, further comprising:

creating refined virtual profile parameters corresponding to the reference signal using the refinement procedure;

verifying that a refined virtual profile creation criteria is met, the refined virtual profile creation criteria comprising a measure of goodness of fit of a simulated signal of a refined virtual profile relative to the reference signal; and extracting refined virtual profile parameters associated with the refined simulated signal that meet the refined virtual profile creation criteria.

33. A system to create a virtual profile library, the system comprising:

a metrology system configured to measure a reference signal off a reference structure on a semiconductor wafer;

a profile evaluator coupled to the metrology system and being configured to compare the reference signal to a plurality of signals in a first library, and to stop the comparison when a first goodness of fit value is met, and to compare the reference signal to a plurality of signals in a second library, and to stop the comparison when a second goodness of fit is met; and a virtual profile evaluator coupled to the metrology system and being configured to create a virtual profile data space when the first and second goodness of fit values are not met, wherein the virtual profile data space is created using differences between a profile data space associated with the first library and a profile data space associated with the second library, to create a first virtual profile signal in the virtual profile data space, to create a virtual profile shape and/or virtual profile parameters based on the first virtual profile signal, to calculate a difference between the reference signal and the created virtual profile signal, to compare the difference to a virtual profile library creation criteria, and to store the first virtual profile signal and virtual profile data, which includes the virtual profile shape and/or virtual profile parameters, associated with the first virtual profile signal when the virtual profile library creation criteria is met, or for applying a corrective action when the virtual profile library creation criteria is not met.

34. A computer readable storage medium containing computer executable code for creating a virtual profile library by instructing a computer to operate as follows:

obtain a reference signal, wherein the reference signal was generated by measuring a signal off a reference structure on a semiconductor wafer;

compare the reference signal to a plurality of signals in a first library, and stop the comparison when a first goodness of fit value is met;

compare the reference signal to a plurality of signals in a second library, and stop the comparison when a second goodness of fit value is met;

create a virtual profile data space when the first and second goodness of fit values are not met, wherein the virtual profile data space is created using differences between a profile data space associated with the first library and a profile data space associated with the second library;

create a first virtual profile signal in the virtual profile data space;

create a virtual profile shape and/or virtual profile parameters based on the first virtual profile signal; and calculate a difference between the reference signal and the first virtual profile signal;

compare the difference to a virtual profile library creation criteria; and either store the first virtual profile signal and the virtual profile data, which includes the virtual profile shape and/or virtual profile parameters, associated with the first virtual profile signal when the virtual profile library creation criteria is met, or applying a corrective action when the virtual profile library creation criteria is not met.

* * * * *